United States Patent [19]

Titus

[11] 4,404,974
[45] Sep. 20, 1983

[54] METHOD AND APPARATUS FOR MONITORING AND DISPLAYING HEART RATE AND BLOOD PRESSURE PRODUCT INFORMATION

[75] Inventor: John S. Titus, Prior Lake, Minn.
[73] Assignee: Possis Medical, Inc., Minneapolis, Minn.
[21] Appl. No.: 291,023
[22] Filed: Aug. 7, 1981
[51] Int. Cl.³ .............................................. A61B 5/02
[52] U.S. Cl. .................................. 128/670; 128/672; 128/696
[58] Field of Search ............... 128/670, 672, 696, 700, 128/710, 713

[56] References Cited

U.S. PATENT DOCUMENTS

| 2,193,945 | 3/1940 | Strauss et al. | 128/2.05 |
|---|---|---|---|
| 2,756,741 | 7/1956 | Campanella | 128/2.05 |
| 3,087,488 | 4/1963 | Streimer | 128/2.05 |
| 3,229,686 | 1/1966 | Edmark, Jr. | 128/2.05 |
| 3,486,499 | 12/1969 | Tsing Ton Yen | 128/2.05 |
| 3,717,140 | 2/1973 | Greenwood | 128/2.05 |
| 3,773,033 | 11/1973 | Rodbard et al. | 128/2.05 |
| 3,831,590 | 8/1974 | Boyle et al. | 128/2.05 |
| 3,908,639 | 9/1975 | McIntyre | 128/2.05 |
| 3,978,848 | 9/1976 | Yen et al. | 128/2.05 |
| 4,112,491 | 9/1978 | Bugay | 364/415 |
| 4,137,910 | 2/1979 | Murphy | 128/2.05 |
| 4,201,222 | 5/1980 | Haase | 128/634 |
| 4,203,451 | 5/1980 | Panico | 128/672 |
| 4,211,238 | 7/1980 | Shu et al. | 128/700 |
| 4,347,851 | 9/1982 | Jundanian | 128/672 |

OTHER PUBLICATIONS

Robinson, B. F., "Relation of Heart Rate and Systolic Blood Pressure to the Onset of Pain in Angina Pectoris", Circulation 35:1073, 1967.
Kitamura, K., Jorgensen, C. R., Gobel, F. L., Taylor, H. L., and Wang, Y., "Hemodynamic Correlates to Myocardial Oxygen Consumption during Upright Exercise", J. Applied Physiology 32:516, 1976.
Jorgensen, C. R., Wang, K., Wang, Y., Gobel, F. L., Nelson, R. R., and Taylor, H., "Effect of Propranolol on Myocardial Oxygen Consumption and its Hemodynamic Correlates during Upright Exercise", Circulation 48: 1173, 1973.
"A monitor for Rate-Pressure Product", by Dennis J. McMahon, B. S., Michael F. Mulroy, M.D., and Robert I. Balfour, M.D., Anesthesiology, 53:508-509, 1980.

Primary Examiner—Richard J. Apley
Assistant Examiner—George Yonulis
Attorney, Agent, or Firm—Burd, Bartz & Gutenkauf

[57] ABSTRACT

A method and apparatus for monitoring and digitally displaying primate heart rate and systolic blood pressure product information. The apparatus has a microprocessor programmed to respond to signals relating to heart rate and systolic blood pressure and provide a digital output of the current product information and a two minute average of the product information. Separate LED displays are used to present the current and two minute average product information. An audible alarm operates to alert the personnel caring for the patient in the event that the pulse rate and blood pressure product exceeds a selected level. Operator controls are operable to read the input values, silence the alarm, read the external preset trip point, read the internal power supply and reference voltages, and verify the operations of all segments of all digits.

62 Claims, 7 Drawing Figures

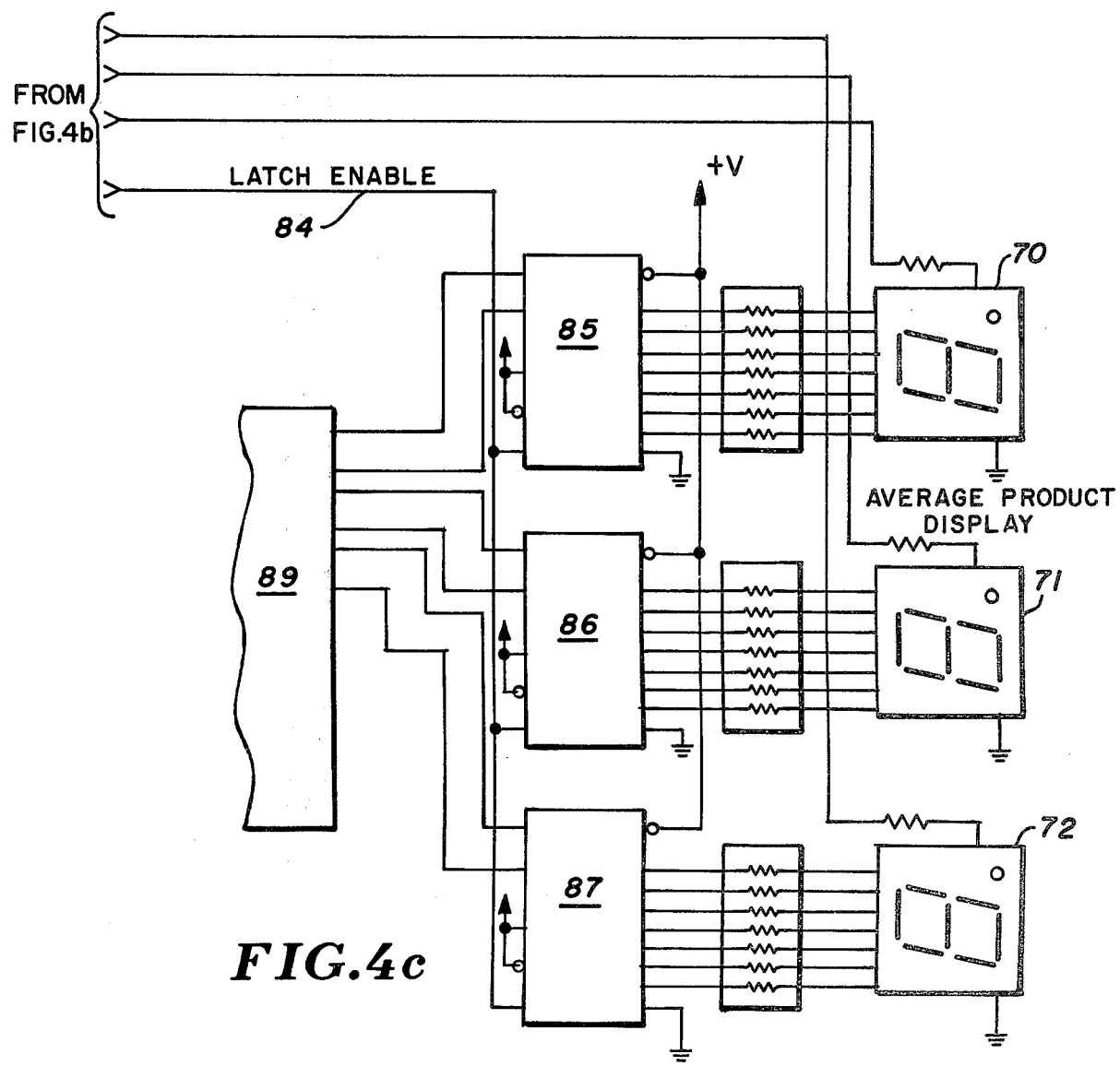

METHOD AND APPARATUS FOR MONITORING AND DISPLAYING HEART RATE AND BLOOD PRESSURE PRODUCT INFORMATION

BACKGROUND OF THE INVENTION

In primate patients undergoing diagnostic and surgical procedures for ischemic heart disease, the assessment of myocardial ischemia is crucial to their safe management. The onset of angina in awake or unsedated patients is a clear indication of ischemia. This indication is not available in patients under sedation or anesthesia. It is to the patient's benefit to prevent situations where the myocardial metabolic requirements exceed the coronary circulation's ability to meet them.

Separate blood pressure monitors and heart rate monitors are used in the operating room to provide instant and continuous readings of the patinet's blood pressure and pulse rate. These separate readings of information relative to the patient's blood pressure and heart rate are mentally combined by the personnel in the operating room to provide rate pressure product information. The rate pressure product information informs the surgeon of myocardial oxygen consumption. The monitoring of the rate pressure product information provides a warning of dangerous increases of myocardial consumption leading to myocardial ischemia or infarction. The rate pressure product mental calculation is periodically made and at times when the operating room personnel are performing critical procedures. Being a mental calculation, it is subject to human error.

SUMMARY OF THE INVENTION

The invention is directed to a method and apparatus for providing heart or pulse rate and systolic blood pressure product information of a primate, as a human, and displaying this information as a continuous current display and a time period average display. The information displayed is the current pulse rate and systolic blood pressure product and the updated two-minute average of the pulse rate and systolic blood pressure product.

If the pulse rate and blood pressure exceeds a selected level, an audible alarm will alert the personnel caring for the patient. Therapeutic intervention can then be administered to the patient to maintain the pulse rate and blood pressure product value within acceptable levels. The apparatus of the invention allows early detection of increased myocardial oxygen consumption. The apparatus also provides pulse rate and blood pressure product information during the therapeutic intervention to lower the oxygen consumption of the heart and thereby prevent initiation of myocardial damage or infarction. The apparatus is useable and compatible with conventioal EKG monitoring and blood pressure monitoring equipment.

The apparatus is an instrument designed to interface to two varieties of popular hospital patient monitor instruments, namely, the variety that provides output in analog form with a range of zero to 2½-volts D.C. representing zero to two hundred and fifty (250) heartbeats per minute or millimeters of mercury systolic blood pressure. An additional interface is provided for a second type of monitor which employs a databus design and transmits patient information in the form of 7-bit bytes of absolute ASCII coded data.

The apparatus provides the ability to display the actual input values of heart rate and systolic blood pressure as interpreted from the analog voltage or read from the databus depending on the type of monitor in question. These two values are multiplied together and a resultant product is displayed in a first 3-digit LED display. A second 3-digit LED display shows a traveling average computed on a two minute window. For the first two minutes the second display will be zero due to the fact that two minutes worth of data are required by the averaging calculation routine.

The apparatus automatically determines which type of patient monitor it is presently connected to by reading one pin of the input connector. If this pin is grounded due to connections in the appropriate cable, the databus mode of operation will be invoked. If the pin is high due to no connection in the input cable, then analog input mode will be invoked. This decision is made on initial start up of the apparatus.

The apparatus has manually actuated controls to control the power and system functions. The controls include an array of buttons operable to read the input values, silence the alarm, read the internal preset trip point, read the internal power supply and reference voltages, and verify the operation of all segments of all digits.

IN THE DRAWINGS

Figure 4A:
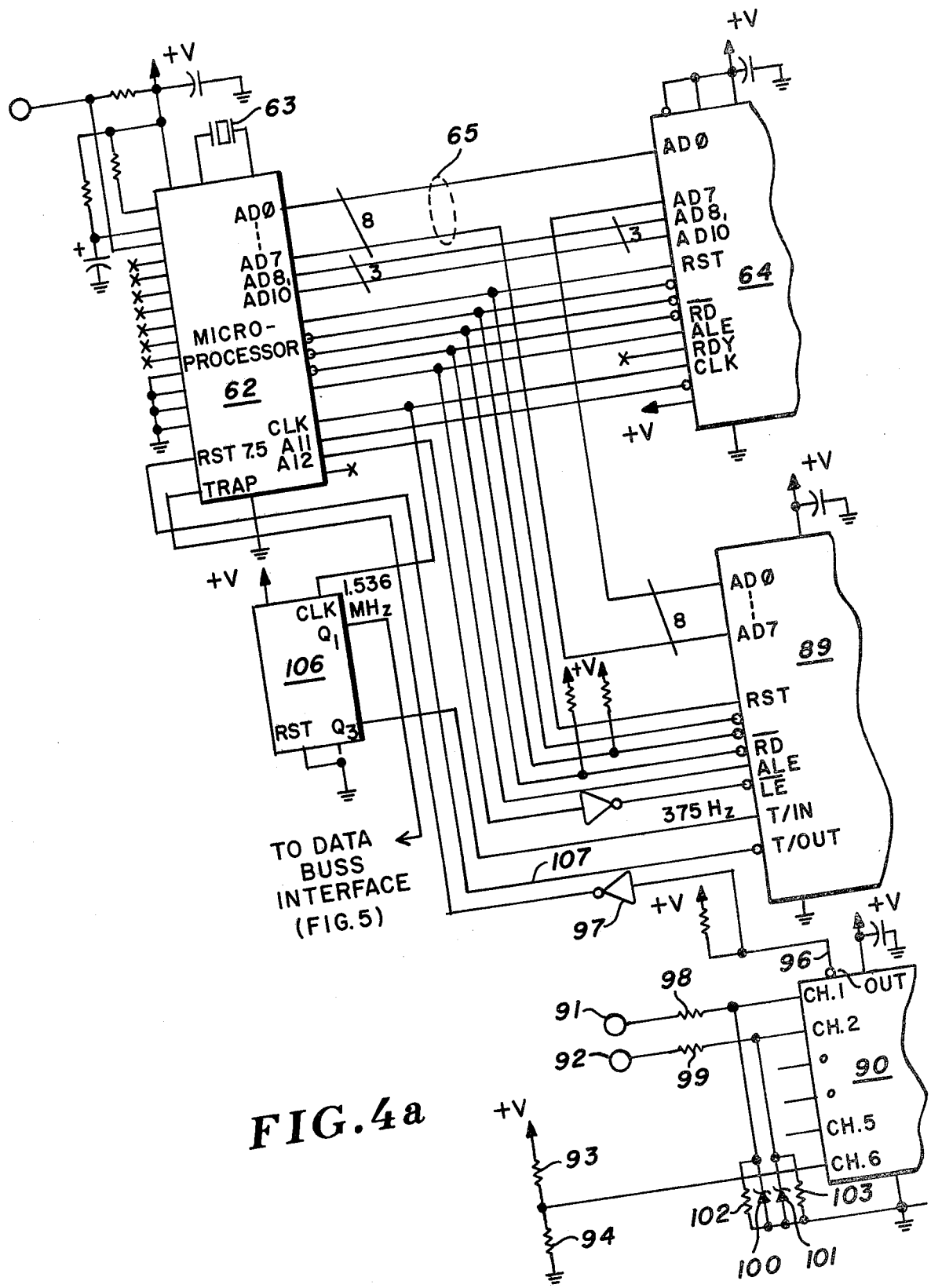
Figure 4B:
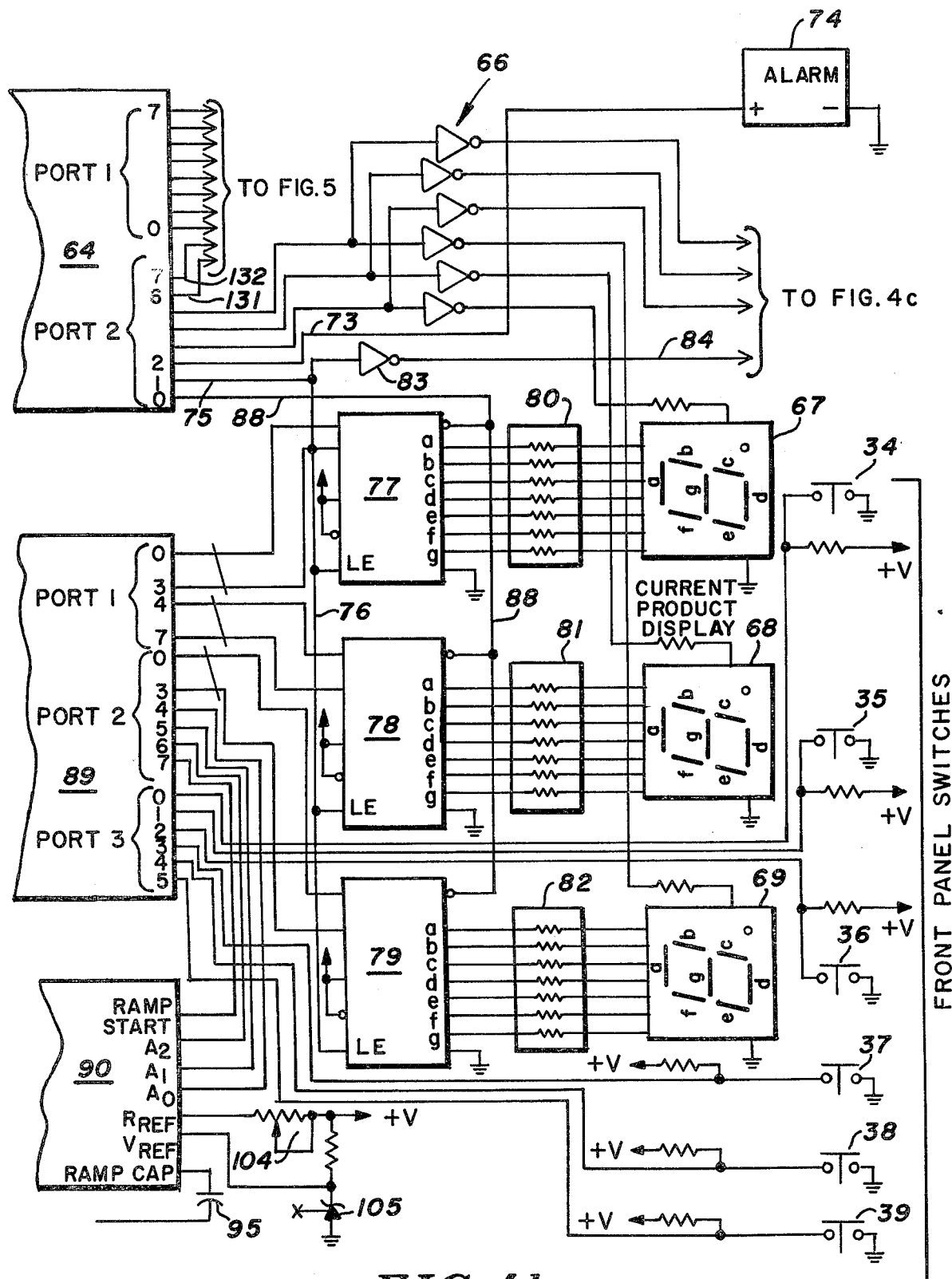
Figure 5:
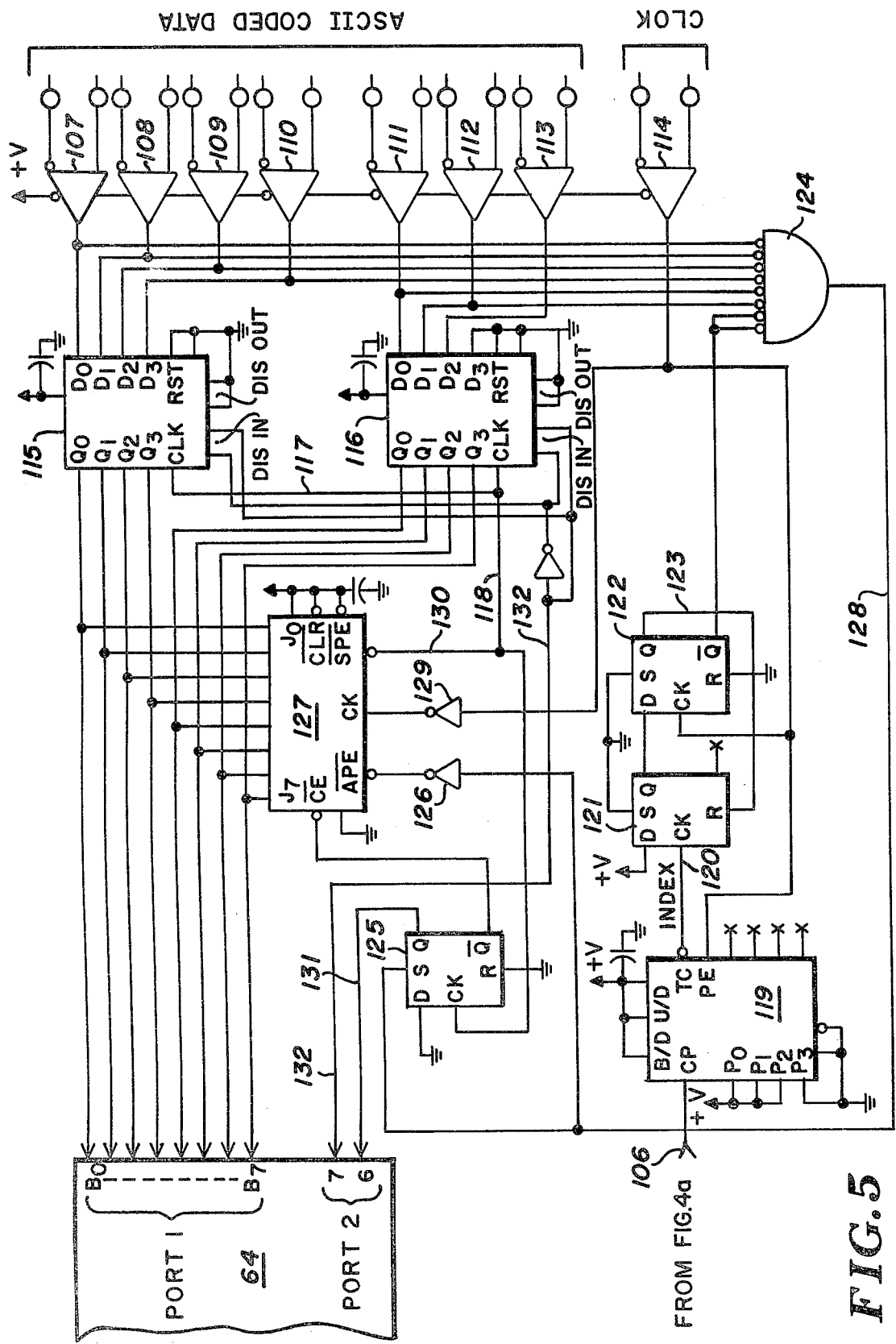

FIGS. 4A, 4B, and 4C are diagrams of the electrical logic circuit of the pulse rate and blood pressure product monitoring and display apparatus; and FIG. 5 is a circuit diagram of a databus interface useable with the pulse rate and blood pressure product monitoring and display apparatus.

DESCRIPTION OF PREFERRED EMBODIMENT

Figure 1:
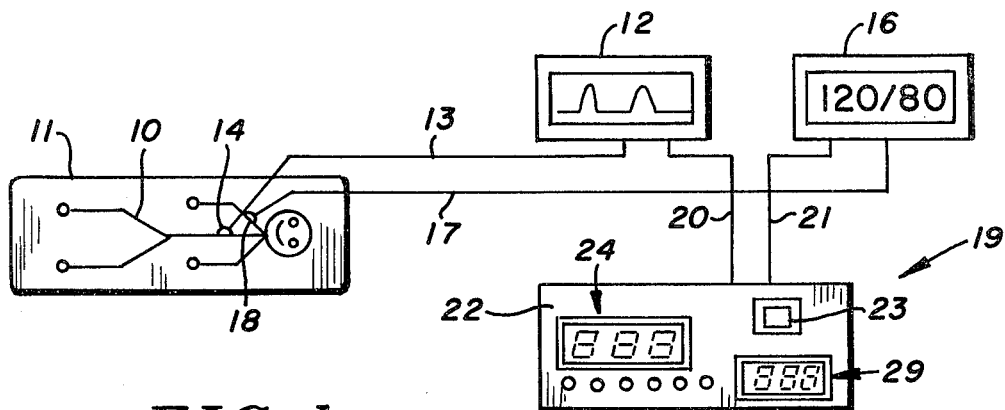
FIG. 1 is a diagrammatic view of a patient coupled to separate pulse rate and blood pressure monitors which are connected to the pulse rate and systolic blood pressure product monitoring and display apparatus of the invention.

Referring to FIG. 1, there is shown a representation of a primate patient 10 lying on an operating table 11 preparatory for surgical procedure for heart disease. The apparatus is described as use with a human patient. The apparatus is useable with other types of primates as well as other animals. Patient 10 is connected to a conventional EKG monitor 12 with a cable 13. The cable 13 is attached to one or more EKG pickup electrodes 14 located in engagement with the body of the patient. Electrodes 14 can comprise a plurality of separate electrodes located in contact with separate parts of the patient.

A blood pressure monitor 16 is connected to the patient via cable 17 and a catheter 18. The catheter has a conventional transducer for sensing the blood pressure of the patient 10. The EKG monitor 12 and blood pressure monitor 16 are conventional instruments that provide outputs in analog form with a range of zero to 2½ volts D.C. The monitors can be of the type that employ databus design and transmits patient information in the form of 7-bits bytes of absolute ASCII coded data.

The pulse rate and systolic blood pressure product monitoring and display apparatus of the invention indicated generally at 19 is electrically coupled to EKG monitor 12 with a cable 20 and to blood pressure monitor 16 with a cable 21. Cables 20 and 21 provide the electrical connections to accommodate the pulse rate electrical signal and blood pressure electrical signal which are transmitted to apparatus 19. Apparatus 19 continuously displays the current pulse rate and systolic blood pressure product. For example, the display for a pulse rate of 66 pulses per minute and systolic blood pressure of 120 mm mercury, the product is 7920 and displays a time period as 2 minute average of the pulse rate and systolic blood pressure product. The blood pressure referred to hereinafter is systolic blood pressure.

Apparatus 19 has a front display panel 22 accommodating an on-off switch 23. A first digital display indicated generally at 24 provides digital information as to the current product of the pulse rate and blood pressure of the patient. Digital display 24 has three numerical LED displays 26, 27, and 28 for displaying the numerical information of the current product of the pulse or heart rate and the systolic blood pressure.

A second digital display indicated generally at 29 mounted on the left corner of panel has three numerical cathode displays 31, 32, and 33 providing information of a two-minute average of the product of the pulse or heart rate and the systolic blood pressure. The electrical logic circuit hereinafter described functions to keep the two-minute average updated every 10 seconds. The time of the average and the update time can be varied as desired.

The panel 22 mounts a plurality of switches 34-39 used to set and control the electrical logic circuits. Switches 34-37 are used to put in a selected product number, which, if exceeded by the product derived from the signal sensed from the patient, will trigger a sound alarm. When switch 34 is actuated the input values upon initial start up or at any other time during the cycle can be read. The blood pressure value is displayed on display 24 and the pulse rate value is displayed on display 29. Upon initial start up, product information or calculated average product information will not be displayed until read input switch 34 has been actuated to verify the accuracy of input data. Switch 35 will silence the sound alarm during the alarm condition if required. Switch 35 is also used with digit buttons to manually put input start up blood pressure data into the memory if monitored blood pressure information is not available. As soon as the appratus 19 has received an actual input data of 30 mm mercury or greater blood pressure, the average calculations will be based on actual data and the manual input start up data disregarded. The third switch 36 is labled "set trip". When switch 36 is depressed, the internal preset trip point will be displayed in display 24. On initial start up the digits will be one hundred sixty (160) representing a rate pressure product of sixteen thousand (16,000). This value is loaded at initial power up of the apparatus 19 as a default value and can be reset to any value desired up to a maximum value of forty-nine thousand nine hundred (49,900) by holding switch 36 depressed. This trip point will then be loaded into the apparatus 19 as soon as the set trip button is released and can be viewed at any time by depressing switch 36 during operation. This value will be reset back to the default value of sixteen thousand (16,000) when the apparatus 19 is powered down and repowered up.

In addition to these operating features, there are three maintenance monitoring switches 37, 38, and 39. If the least significant digit select switch 39 is held depressed during operation of the apparatus 19, the internal power supply voltage will be displayed on display 24. If the center digit switch 38 is depressed and held down, the internal reference voltage used by the analog to digital circuitry will be displayed on display 24. If the most significant digit switch 37 is held depressed, all eights will be displayed in both displays 24 and 29 in order to verify the operation of all segments of all digits to prevent misinterpretation of numerical output due to a burned out segment.

Figure 3:
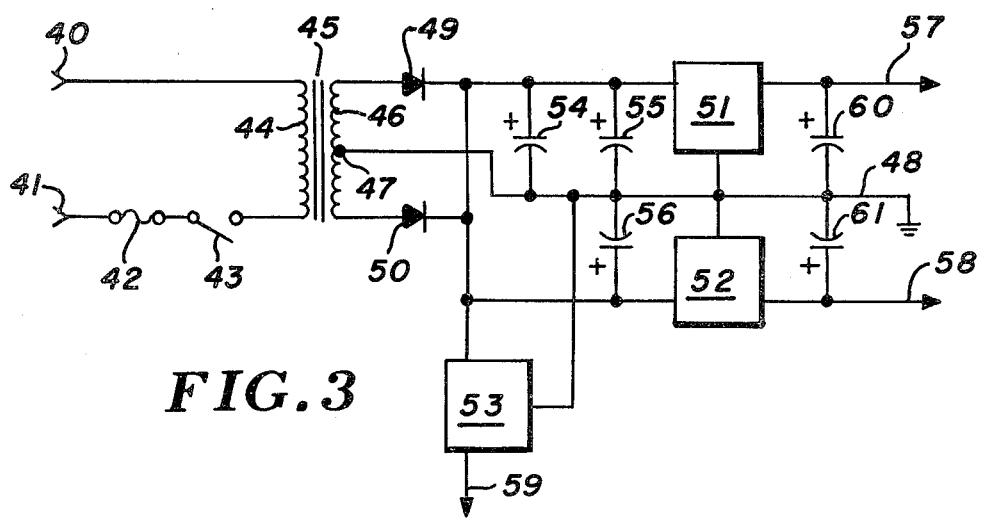
FIG. 3 is a circuit diagram of the power supply of the apparatus.

Referring next to FIG. 3, there is illustrated by means of a schematic diagram the power supply circuit used to develop the required regulated voltages necessary for proper operation of the apparatus 19. The terminals 40 and 41 are adapted to be connected to a source of 120 volt, 60-cycle alternating current voltage. Terminal 41 is coupled through a fuse 42 and a single pole, single throw switch 43 to one side of a primary winding 44 of a power supply transformer 45. The remaining terminal of the primary winding 44 is directly connected to the supply terminal 40. Transformer 45 has a secondary winding 46 which is center tapped at 47 and this center tap terminal is connected to a ground bus 48. First and second diodes 49 and 50 have their anode terminals connected to the opposed outside terminals of the secondary winding 46 and their cathode electrodes tied in common with one another and to the input terminals of a plurality of integrated circuit-type voltage regulators 51, 52, and 53. Coupled between the input terminals of the voltage regulators 51 and 52 and the ground bus 48 are filer capacitors 54, 55, and 56.

The transformer 45 may have a turns ratio such that the voltage developed across its secondary winding may be 10 volts AC. The voltage regulators may then comprise Type LM7805 integrated circuits which are available from the National Semiconductor Company of Santa Clara, Calif. The LM7805 series voltage regulator is a three terminal device having a fixed output voltage of 5 volts. Furthermore, it is capable of providing an output current in excess of 1 ampere. The ground terminal of each of the regulator devices 51-53 is connected to the ground bus 48. The regulated output voltage appears at the output terminals 57, 58, and 59 with a Type LM7805 regulator, this output voltage will be effectively maintained at a 5 volt level. As will be explained in greater detail hereinbelow, the output from the voltage regulator 51 appearing at terminal 57 provides $V_{cc}$ to the microprocessor circuits used in the implementation of the present invention, the output of the regulator 52 appearing at terminal 58 provides the $V_{cc}$ to the data bus interface circuit while the output from the third regulator 53 appearing at terminal 59 provides a 5-volt potential to the display circuits used to visually present the rate pressure product and other parameters.

The capacitors 60 and 61 connected between the ground bus 48 and the output terminals 57 and 58 respectively provide further smoothing and elimination of any ripple signal from the regulated DC output voltages.

While Type LM7805 integrated circuit regulator devices have been found suitable in implementing the power supply portion of the present invention, it is, of course, to be understood that such choice is not intended to be limitative, but only illustrative.

FIGS. 4A, 4B, and 4C together present a schematic electrical diagram of the microprocessor system and the display portion of the apparatus 19 of the present invention. The microprocessor itself is an integrated circuit chip and is identified by numeral 62 in FIG. 4A. In implementing the present invention, it was found convenient to employ an INTEL Type 8085A microprocessor and the explanation of the invention will continue with that chip as the illustrative example of a suitable microprocessor which may be employed in implementing the system. However, limitation to that particular integrated circuit microprocessor is not intended and should not be inferred.

The microprocessor 62 is provided with an external crystal 63 which cooperates with the internal clock circuitry designed into the microprocessor chip to generate a clock frequency of, say, 6.144 megahertz.

Program storage for the microprocessor 62 is provided by a programmable read-only memory 64. A suitable integrated circuit chip which is compatible with the INTEL 8085A microprocessor is a Type 8755A erasable, programmable, read-only memory integrated circuit, also available through the INTEL Corporation. An 8-bit address bus is connected between the address output terminals AD0 through AD7 of the microprocessor chip 62 and the correspondingly labeled address input terminals AD0 through AD7 of the PROM device 64.

With reference to FIG. 4B, the PROM device 64 has two 8-bit input/output ports labeled port 1 and port 2. Port 1, bits 0–7 are arranged to be coupled to the external patient monitor data bus shown in FIG. 5. Port 2 is an internal control port with the two highest order bits thereof (bits 6 and 7) also being coupled to the data bus interface of FIG. 5. Bits 3, 4, and 5 of port 2 of the PROM 64 are coupled through a set of inverters indicated generally by numeral 66 to control the illumination of the decimal point LED on the seven segment display elements 67, 68, and 69 of FIG. 4B and on the seven segment display elements 70, 71, and 72 of FIG. 4C. The display elements 67, 68, and 69 on FIG. 4B comprise the "orange" display used to present the current product of pulse rate and systolic blood pressure. The display elements 70, 71, and 72 on FIG. 4C comprising the green display are used to present the average of this product over a two minute interval.

Bit 2 of the I/O port 2 of the PROM device 64 has a conductor 73 coupling it to an alarm device 74. In the preferred embodiment the alarm device 74 comprises a high frequency tone generator which is turned on by a logical "high" signal on the bit 2 output of the control port 2 of the PROM 64. Thus, when the pulse rate and blood pressure product exceeds a value programmed into the apparatus 19, the alarm device 74 will provide an audio or visual indication of that fact.

Bit 1 of port 2 is tied directly by conductors 75 and 76 to the Latch Enable inputs of a set of BCD-to-7 bar latch/decoder/driver integrated circuit devices including those identified by numerals 77, 78, and 79 in FIG. 4B. In implementing the preferred embodiment, Type CD4511 IC's manufactured and sold by the National Semiconductor Company of Santa Clara, Calif. may be utilized. It is a complementary MOS enhancement mode device and includes NPN bipolar output drivers in a single monolithic structure. Each of the circuits 77 through 79 provides the function of a 4-bit storage latch, an 8-4-2-1 BCD-to-seven segment decoder, an an output drive capability. An appropriate signal on the Latch Enable input allows a BCD code to be stored. By coupling the outputs of the device to suitable display elements such as seven-segment LED's or to liquid crystal read-out devices, the bars defining the character to be displayed are illuminated as a function of the BCD value stored.

The outputs from the latch/decoder/driver 77 through 79 are coupled through banks of current limiting resistors 80, 81, and 82 to corresponding input terminals of the display devices 67, 68, and 69. Depending upon the bit permutations of the outputs a through g, the corresponding bars of the display devices 67–69 will be illuminated.

The output from bit 1 of port 2 of the PROM device 64 is also coupled through an inverter 83 and the conductor 84 to a set of BCD-to-seven segment latch-/decoder/drivers 85, 86, and as shown 87 in FIG. 4C. These may likewise comprise Type CD4511 IC devices and operate in a fashion identical to circuits 77, 78, and 79, except that they are used in conjunction with the "Average Product" or green display elements 70, 71, and 72 in FIG. 4C. Because of the manner in which the Latch Enable control signals on conductors 76 and 84 are developed, either the Current Product display or the Average Product display will be enabled in that the signal on line 76 is always the inverted version of that on the conductor 84.

Bit 0 of port 2 of the PROM device 64 is coupled by way of conductor 88 to the Blank terminal of the IC's 77, 78, and 79 and when this signal is low, the display elements 67, 68, and 69 will be blanked, irrespective of the digital value which may be latched in the BCD-to-seven segment driver.

The microprocessor employed in the apparatus 19 also utilizes random access storage in the form of the IC RAM device 89. In the preferred embodiment, a Type 8155 IC chip manufactured and sold by the INTEL Corporation has been utilized. This chip contains 256 bytes of random access memory along with an internal programmable timer, two 8-bit I/O ports and one 6-bit I/O port.

As is indicated in FIG. 4B, the first 8-bit I/O port controls the display digits of the two least significant digits of both the Current Product display (FIG. 4B) and the Average Product display (FIG. 4C). The lower 4-bits of I/O port number 2 of the RAM 89 controls the most significant digit numerals in both the Current Product display and the Average Product display. The higher ordered 4-bits of port number 2 of the RAM are connected as control inputs to an analog-to-digital converter which comprises the integrated circuit chip 90 in FIGS. 4A and 4B. In implementing the system of the present invention, it has been found convenient to employ a Type MC14443 A/D converter; however, other integrated circuit devices are available on the market for performing this function and can be used as well. The manner in which the A/D device operates in the present system will be set forth in greater detail hereinbelow, but before describing that operation, the remaining outputs from the RAM device 89 will be described.

Figure 2:
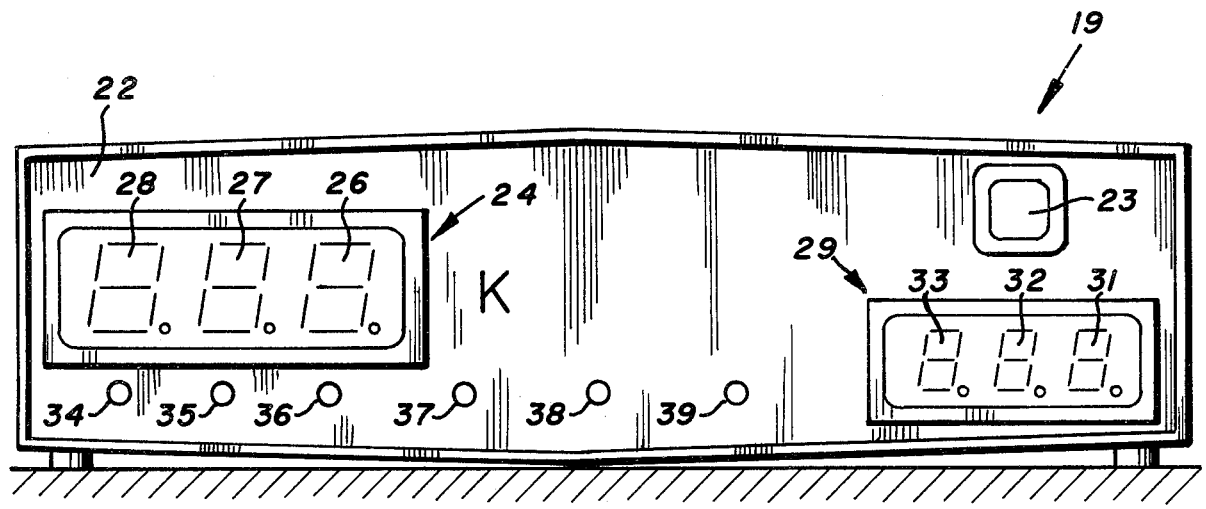
FIG. 2 is a front view of the display panel of the pulse rate and blood pressure monitoring and display apparatus of FIG. 1.

The 6-bit port, i.e., port 3 on the RAM 89, provides an input to the microprocessor chip 62 from the 6 control push-button 34–39 located on the front panel of the monitor cabinet as shown in FIG. 2. Thus, the first Set Digit push-button 34 may be used to apply an input signal to bit 0 of port 3, that signal either being a plus voltage or ground, depending upon the actuation of the push-button. In a similar fashion, the Set Digit push-buttons 35 and 36 are used to apply input signals to bits 1 and 2 of port 3. Bits 3, 4, and 5 of port 3 are respectively coupled to the "Set Trip" push-button 37, the "Silence Alarm" push-button 38 and the "Read Inputs" push-button 39. In each instance, the signal applied to bits 3, 4, and 5 of port 3 is either a positive voltage, +V, or ground depending upon whether the switches 37–39 are open or closed.

As has been indicated previously, the A/D converter 90 is preferably a Type MC14443 integrated circuit device manufactured and sold by Motorola Semiconductor Products, Inc. and, with this in mind, the inputs $A_2$, $A_1$, and $A_0$ arriving from bits 4, 5 and 6 of port 2 of the RAM device 89 comprise addressing inputs for selecting which of the particular input channels 1 through 6 is operational. The input analog voltage to be converted to a digital code is applied to the input channels and, in this regard, an analog signal proportional to heart rate may be applied to the terminal 91 while the analog voltage proportional to systolic blood pressure may be applied to the channel 2 input terminal 92. A reference current is applied to the channel 6 input by way of a voltage divider including the series connected resistors 93 and 94 which connect between a source of voltage +v and ground. Contained within the IC chip 90 are a one of eight decoder, an eight channel analog multiplexer, a buffer amplifier, a precision voltage to current converter, a ramp start circuit, and a comparator. The output driver of the comparator is an open-drain N-channel which is capable of sinking up to 5 mA of current. The microprocessor system provides the addressing, timing, counting and arithmetic operations required for implementing a full analog-to-digital conversion system.

Once the particular channel 91 or 92 has been selected by the appropriate inputs to the address terminals $A_0$ through $A_2$ has been completed, the voltage present at the selected input is used to charge the ramp capacitor 95 which may typically be a 0.1 microfarad Mylar capacitor. After a slight delay, the Ramp Start pin of the A/D chip is made to go high. The microprocessor is simultaneously put into a very tight counting loop so as to count the number of cycles through this loop that are required in order to have the capacitor 95 discharge sufficiently to generate an output signal from the Output terminal 96 of the A/D chip. This output signal is inverted by inverter 97 and applied to the microprocessor as a Trap input which is effective to generate an interrupt.

At the moment that the interrupt signal occurs, the microprocessor samples and retains the number of counts through the internal loop and thereby accumulates a relative digital number which is proportional to the amplitude of the input analog voltage presented to the selected channel of the A/D chip at the beginning of the cycle. As was mentioned, an analog signal proportional to heart rate and to systolic pressure are applied, respectively, to channels 1 and 2 by way of input terminals 91 and 92. These signals are isolated by the resistors 98 and 99 and the input terminals of the A/D chip are protected from over-voltage by the zener diodes 100 and 101 and their associated parallel resistor elements 102 and 103. The resistors 102 and 103 are connected between the input pins for channels 1 and 2 of the A/D chip and ground and therefore provide a ground potential for the inputs when they are not in use.

The terminal labeled $R_{ref}$ of the chip 90 is connected to a potentiometer 104 which is referenced to the system's $V_{cc}$. The potentiometer may be used to trim the A/D chip for proper ranging. A precision reference voltage is furnished by the zener diode 105. Because channel 7 of the chip is internally connected to the reference voltage while channel 0 is internally connected to ground, both ground and reference voltage measurements may be made by the microprocessor for referencing purposes when desired.

Typically, in operation, the A/D chip 90 has Address Input Select signals applied to the terminals $A_0$ through $A_2$. Depending upon the bit permutations of these signals, channels 0, 1, 2 or 7 may be selected. Channels 3 through 5 are unused. When the Ramp Start terminal is low, the ramp capacitor 95 is charged to a voltage associated with the selected input channel. When the Ramp Start is brought high, the connection to the input channel is broken and the capacitor 95 begins to ramp towards $V_{cc}$. The ramp capacitor is, of course, used to generate a time period when discharged from a selected voltage by way of a precise reference current maintained at channel 6. The reference current which discharges the ramp capacitor is fixed by way of a precision resistor network (potentiometer 104) to the positive supply. The comparator output signal on line 96 is low when the ramp capacitor has reached the discharged voltage and is high otherwise. The reference voltage $V_{Ref}$ obtained at the cathode of the zener diode 105 comprises a known voltage to which the unknown analog input is compared.

Timing for read and write cycles in the RAM 89 is controlled by an internal timer which is driven by the output of a predetermined stage of a frequency divider 106. Specifically, the frequency divider 106 receives as its input, clock pulses from the microprocessor chip 62. Typically, the frequency of the clock pulses applied to the divider may be 3.072 magahertz. If a Type CD4020 frequency divider is employed as in the preferred embodiment and the output of the RAM is obtained at the output of stage $Q_{13}$, then the frequency of the pulses applied to the RAM 89 will be 375 Hz.

The timer output from the RAM 89 is programmably adjustable and is returned to the RST 7.5 interrupt input of the microprocessor chip 62 by way of the conductor 107. This interrupt may occur every ½ second and is used as a basic timing pulse for the real-time functions of the Rate Pressure Product Monitor.

DATA BUS INTERFACE

The monitor device of the present invention incorporates an external differential data bus which is illustrated in block diagram form in FIG. 5 of the drawings. It may include two Type 3486 differential receiver integrated circuit chips for receiving patient information in the form of seven-bit bytes of absolute ASCII coded data. Thus, different types of external monitoring equipment may be used with the system of the present invention. Type 3486 IC's, being quad-type devices, are capable of receiving the seven bits of the ASCII coded data and also have a hysteresis type amplifier embodied therein for handling clock signals. The ASCII inputs are applied to the tri-state buffer amplifiers 107 through 113 with the clock information being applied to the tri-state buffer amplifier 114. The output from the amplifiers 107 through 110 are individually coupled to the four inputs of a tri-state quad D flip-flop 115. In a similar fashion, the three highest order bits of the seven-bit ASCII coded data from buffer amplifiers 111 through 113 are applied to a second tri-state quad D flip-flop integrated circuit 116. These two flip-flops function to latch the data on the input lines upon the occurrence of a clock input thereto, via conductors 117 and 118. The manner in which this clock pulse is generated will now be explained.

The actual bus decoding is accomplished in several steps which involve a combination of hardware and software. The first step involves the decoding of each repetitive bus cycle. The bus clock functions to generate a missing pulse at the beginning of each of fourty-eight cycles. This missing pulse is detected by a presettable counter integrated circuit 119 which is operated at a clock frequency of 1.536 MHz derived from the frequency divider 106 of FIG. 4A. The counter 119 is respectively reset to zero by the bus clock. However, when the Bus Clock Missing pulse is detected, counter 119 is able to reach its terminal count and it generates an Index pulse on conductor 120.

The Index pulse on conductor 120 is applied to a D-type flip-flop, such as a Type CD4013 dual D flip-flop manufactured and sold by the National Semiconductor Company of Santa Clara, Calif. In this device, the logic level present at the "D" input is transferred to the Q output during the positive-going transition of the applied clock pulse. Setting or resetting is independent of the clock and is accomplished by applying a high logic signal on the set or reset line respectively. Hence, with the arrangement illustrated, the index pulse, produced when the presettable counter 119 times out, clocks the flip-flop 121 whose Q output is tied to the data input of a similar D-type flip-flop 122. The next data clock pulse passing through the buffer amplifier 114 causes the high signal to be transferred to the Q output of the flip-flop 122 and it is fed back, via conductor 123, to reset the first flip-flop 121. The resulting delayed Q output comprises a delayed index pulse. It is fed into an eight-input negative AND gate 124. The remaining inputs to this negative AND gate come from the outputs of amplifiers 107 through 112 which constitute the appropriate data bus signals to decode the $0^{th}$ position of the bus, providing an output pulse at the beginning of the $0^{th}$ of the 48 bus output cycles. This output pulse is first used to set the Count Duration flip-flop 125 which may also be a D-type flip-flop. After passing through inverter 126, the same output pulse is used as the asynchronous preset enable (APE) signal for the presettable integrated circuit counter 127. The counter 127 preferrably comprises a Type 40103 8-bit presettable counter having jam inputs J0 through J7 coupled to the output lines of the tri-state quad D flip-flop latch circuits 115 and 116. These same outputs are connected as inputs to the PROM 64 and specifically to bits 0 through 7 of port 1 thereof. When the negative AND gate 124 is fully enabled by having low signals on all of its inputs, a high output signal is produced on the conductor 128 and when this high signal is fed through the inverter 126 previously mentioned, a low APE signal is applied to the presettable counter 127. This causes the binary value stored in the quad D flip-flop 115 and 116 to be entered into the counter 127.

It can be seen, then, that the counter 127 is preset by an output number from the PROM 64 data bus port 1. The data bus clock applied through the buffer amplifier 114 and through the inverter 129 is then used to increment the counter 127 until the preset number is reached. At this time, an output pulse is provided by the counter on conductor 130 which is effective to clock the D-type flip-flop 125 causing its Q output on line 131 to go low. All the while, the microprocessor chip 62 has been monitoring the line 131 which is the input to bit-6 of the control port (port 2) of the PROM device 64. As long as this line is high, the counter 127 is in the process of counting. When the line 131 goes low, the presettable counter 127 has reached its terinal count. The Q output from the data flop 125 will also go high at this time and, when applied to the count enable input CE of the counter 127 will preclude that counter from continuing to be advanced by the data bus clock signals.

The Terminal Count output pulse on line 130 also is routed to the clock inputs of the two quad D flip-flops 115 and 116 allowing them to latch the data existing on the data bus at the moment that the terminal count signal on line 130 goes low. Therefore, when the microprocessor senses that counting has ceased through its monitoring of bit-6 of the control port 2 on the PROM device 64, it drives the output from bit-7 of this same control port low to thereby place the latch circuits 115 and 116 in the read mode and enables the microprocessor chip to read the data that had been present on the data bus at the moment of latching through the data bus port (port 1) of the PROM device 64. In this fashion, the individual ASCII digits from external equipment tied to the data bus are read by the microprocessor, one at a time, and then re-assembled by the microprocessor's software to thereby reconstruct the numerical information being presented by the data bus. In that the data bus transfer rate is significantly faster than the microprocessor would otherwise be able to directly read and decode the information, the foregoing method for sampling the data bus and assembling the transmitted data words is necessitated.

It may be noted that the information on the bus could be in a state of transition because of a numerical change occurring during the bus read cycle. To obviate the possible introduction of an erroneous message, the microprocessor first reads all of the digits of a number, temporarily stores them and then reads all of the digits on the data bus a second time. It compares the stored value with the latest value read and if the two numbers match, then it is recognized that the number originally stored is valid. However, if the two numbers do not agree, an additional number is read from the bus and so on until two consecutive numbers are read that do match. By thus verifying the numerical data, the possibility of entering false readings into the monitoring software is precluded.

The PROM device 64 provides program storage whereby all system functions are carried out through execution of the program. Either an analog voltage in the range from 0 to −2.5 volts is applied to the analog voltage input terminals 91 and 92 of FIG. 4A or bus data in ASCII format from a patient monitor provide heart rate data and systolic blood pressure data. Where an analog input signal is employed, it is converted to a digital value and made available to the arithmetic circuits within the microprocessor chip 62. The ASCII data is already in a digital form and may be entered into the PROM device 64 a byte at a time in the manner previously described.

Irrespective of the manner in which the heart rate and blood pressure data are made available to the monitor system of the present invention, the two values are multiplied and the product is compared to an adjustable set-point. If the set-point is reached, an alarm will sound and the current product display will flash the computed product until reset. Where desired, the alarm may be silenced through the actuation of the push-button 38. The display consisting of display elements 70, 71, and 72 is used to present a digital value indicative of the average value of the heart rate times blood pressure product over the immediately preceding two minute time interval. Following the power-up operation, however, the "average display" will present 0's for the first two minutes of operation. The product will not be up-dated so long as the input heart rate remains less than 35 beats per minute. The actual input blood pressure and heart rate may be displayed when commanded by operation of the Read Inputs push-button 39 on FIG. 4B.

The system of the present invention permits a preliminary systolic pressure to be entered at start-up if a monitored value is not then available. When a monitored pressure of 35 mm of mercury is reached, the value being monitored will automatically be substituted for the preliminary systolic pressure originally entered.

The hardware implementation for carrying out the foregoing functional operations has already been set forth. Set out below is the copyrighted software program which is entered into the PROM. Under control of the microprocessor, the various instructions comprising the program are read out in a prescribed order into the microprocessor and used to effect data transfers and computations whereby the above-described mode of operation is realized. The Commissioner of Patent and Trademarks is authorized to reprint the copyright software program in the U.S. Patent issued from this application and copies thereof.

It is to be understood, however, that those skilled in the art will be able to arrive at alternative programming sequences from that set forth and that it is not intended that the program listings indicated be limitive but only exemplary of a preferred mode of operation.

```
; THIS PROGRAM RESIDES IN PROM MEMORY IN THE RPPM AND CONTROLS
; ALL SYSTEM FUNCTIONS.  A 0 - 2.5 VOLT INPUT VOLTAGE OF BUS DATA
; FROM A PATIENT MONITOR FOR BOTH HEART RATE AND SYSTOLIC PRESSURE
; ARE MULTIPLIED AND THE PRODUCT IS COMPARED TO AN ADJUSTABLE SET
; POINT.  IF THE SET POINT IS REACHED, AN ALARM WILL SOUND AND
; THE DISPLAY WILL FLASH THE CONTINUED PRODUCT UNTIL RESET.
; THE ALARM MAY BE SILENCED IF DESIRED BY PUSHBUTTON.
; A SECOND SMALLER DISPLAY SHOWS THE AVERAGE PRODUCT OVER THE
; PAST CURRENT 2 MINUTE PERIOD.  THE AVERAGE DISPLAY IS 0'S FOR
; THE FIRST 2 MINUTES OF OPERATION.
; THE PRODUCT WILL NOT BE UPDATED SO LONG AS THE INPUT HEART RATE
; IS LESS THAN 35 BEATS PER MINUTE.
; THE ACTUAL INPUT PRESSURE & RATE ARE DISPLAYED WHEN COMMANDED
; BY PUSHBUTTON, & MUST BE SO DISPLAYED BEFORE ALLOWING SYSTEM
; OPERATION ON INITIAL POWER-UP.
; A PRELIMINARY SYSTOLIC PRESSURE MAY BE ENTERED AT START-UP IF A
; MONITORED VALUE IS NOT YET AVAILABLE.
; WHEN A MONITORED PRESSURE OF 35 MM HG IS REACHED, THE MONITORED
; VALUE WILL BE AUTOMATICALLY SUBSTITUTED.
; ALL DECIMAL POINTS WILL FLASH WHEN A TO D INPUT IS OVER 2.50 VDC.

TITLE    'Rate Pressure Product Monitor Program rev D'

MACLIB   I8085              ; USE 8085 MACRO LIBRARY FOR RIM & SIM

; SYSTEM EQUATES

0000 =    CNTRLPT   EQU    00H        ; DISPLAY & BEEPER CONTROL PORT
0001 =    DATAPT    EQU    01H        ; EXTERNAL BUS COMMUNICATIONS PORT
0002 =    CNTRLDDR  EQU    02H        ; DATA DIRECTION REG. FOR CONTROL PORT
0003 =    DATADDR   EQU    03H        ; DATA DIRECTION REG. FOR DATA PORT
0018 =    COMDSTRG  EQU    18H        ; COMMAND-STATUS REG. FOR 8155
0019 =    LSDPT     EQU    19H        ; LSD & MID OUTPUT PORT
001A =    MSDPT     EQU    1AH        ; MSD OUTPUT PORT
001B =    SWPT      EQU    1BH        ; SWITCHES INPUT PORT
001C =    TIMLOBYT  EQU    1CH        ; TIMER LOW BYTE PORT
001D =    TIMHIBYT  EQU    1DH        ; TIMER HIGH BYTE PORT
1800 =    RAMSTART  EQU    1800H      ; START OF SYSTEM RAM
1800 =    RS        EQU    RAMSTART
1800 =    OVFLFLG   EQU    RS         ; A TO D OVERFLOW FLAG

; THE GROUP OF FLAGS FROM RS+1 TO RS+6 ARE THE SWITCH FLAGS

****
1801 =    LSDFLG    EQU    RS+1       ; FLAG TO INCREMENT LSD
```

CP/M MACRO ASSEM 2.0    Rate Pressure Product Monitor Program rev D

```
1802 =          MIDFLG      EQU     RS+2        ; FLAG TO INCREMENT MID
1803 =          MSDFLG      EQU     RS+3        ; FLAG TO INCREMENT MSD
1804 =          TRIPFLG     EQU     RS+4        ; FLAG TO SHOW TRIP PT
1805 =          SLBEPFLG    EQU     RS+5        ; FLAG TO SILENCE ALARM & SHOW MDI PRES
1806 =          INPUTFLG    EQU     RS+6        ; FLAG TO SHOW INPUTS
                ****

1807 =          BLNKFLG     EQU     RS+7        ; FLAG TO BLINK DISPLAY & ALARM
1808 =          OFONFLG     EQU     RS+8        ; FLAG TO SILENCE ALARM
1809 =          ALMFLG      EQU     RS+9        ; FLAG TO INVOKE ALARM
180A =          LSDSFLG     EQU     RS+10       ; FLAG TO TOGGLE LSD
180B =          MIDSFLG     EQU     RS+11       ; FLAG TO TOGGLE MID
180C =          MSDSFLG     EQU     RS+12       ; FLAG TO TOGGLE MSD
180D =          MULTFLG     EQU     RS+13       ; FLAG TO SIGNAL 1 SEC. MULTIPLY
180E =          AVGFLG      EQU     RS+14       ; FLAG TO DISPLAY AVERAGE
180F =          STARTFLG    EQU     RS+15       ; FLAG TO START AVERAGING (LESS 2 MIN.)
1810 =          GOFLG       EQU     RS+16       ; FLAG TO ENABLE SYS AFTER READ INPUTS
1811 =          BUSFLG      EQU     RS+17       ; FLAG TO SWITCH INPUTS TO BUS SYSTEM
1812 =          AVGCNT1     EQU     RS+18       ; 1 BYTE FOR FIRST AVERAGE LIST COUNTER
1813 =          AVGCNT2     EQU     RS+19       ; 1 BYTE FOR SECOND AVERAGE LIST COUNTER
1814 =          AVGSAVE     EQU     RS+20       ; 1 BYTE FOR AVERAGE STORAGE
1815 =          SECCOUNT    EQU     RS+21       ; 1 BYTE FOR SECOND COUNTER
1816 =          STARTCNT    EQU     RS+22       ; 1 BYTE FOR INNITAL (2 MIN.) STARTUP
1817 =          WATCHFLG    EQU     RS+23       ; 1 BYTE FOR WATCHDOG CYCLE COUNTER
1818 =          BCDSAVE     EQU     RS+24       ; 5 BYTES FOR BCD STORAGE
181D =          TRIP        EQU     RS+29       ; 2 BYTES FOR TRIP PT STORAGE
181F =          PSAVE       EQU     RS+31       ; 2 BYTES FOR PRODUCT STORAGE
1821 =          SAVPNTR     EQU     RS+33       ; 2 BYTES FOR AVG LIST POINTER
1823 =          PRSAVE      EQU     RS+35       ; 2 BYTES FOR MDI PRESSURE STORAGE
1825 =          AVGTABLE    EQU     RS+37       ; 12 BYTES AVERAGING LIST

18FF =          RAMTOP      EQU     18FFH       ; TOP OF RAM (STACK LOCATION)

; FIRST INNITALIZE THE HARDWARE

0000            START:  ORG     000H

0000 F3         STARTUP: DI                     ; DISABLE INTERRUPTS
0001 31FF18             LXI     SP,RAMTOP       ; TOP OF RAM
0004 3EBF               MVI     A,1011$1111B    ; ALL BITS BUT B6 SET TO OUTPUT
0006 D302               OUT     CNTRLDDR        ; DDR FOR PORT 0H
0008 3E03               MVI     A,03H           ; PORTS 19&1A OUT, 1B IN
000A D318               OUT     COMDSTRG        ; CSS FOR PORTS 19,1A&1B
000C 3E00               MVI     A,0
000E D319               OUT     LSDPT           ; ZERO DISPLAY &
0010 D31A               OUT     MSDPT           ; ANALOG INPUTS
0012 3EB9               MVI     A,1011$1001B    ; TURN OFF DP'S, SET DATABUS TO LATCH
0014 D300               OUT     CNTRLPT         ; MODE & TURN ON DISPLAY
0016 AF                 XRA     A               ; BYTE TO CLEAR FLAGS
0017 214618             LXI     H,RAMSTART+70   ; TOP OF VARIABLE AREA TO BE 0'ED
001A 77         ZEROFLG: MOV    M,A             ; PUT A IN RAM
001B 2D                 DCR     L               ; DECREMENT RAM & COUNTER
001C C21A00             JNZ     ZEROFLG         ; DO ANOTHER IF NOT 0
001F 77                 MOV     M,A

; JUMP TO THE SETUP ROUTINE FROM HERE

0020 C32700             JMP     SETUP

; *TRAP* THE PROCESSOR JUMPS HERE (24H) WHEN THE TRAP
```

; INPUT PIN GOES HIGH. JUMP TO INTERRUPT SUBROUTINE.

```
0024                    ORG     START+24H
0024 C34104             JMP     TRAPPED
```

; SETUP LOADS THE DEFAULT VALUES IN RAM

```
0027 21803E    SETUP:   LXI     H,16000             ; TRIP PT DEFAULT VALUE
002A 221D18             SHLD    TRIP
```

; INNITALIZE HARDWARE TIMER TO PROVIDE 1/2 SECOND INTERRUPTS

```
002D 3EC0               MVI     A,1100$0000B        ; 00H & TIMER MODE 4
002F D31D               OUT     TIMHIBYT            ; CONTINUOUS PULSES 1/2 SEC
0031 3EBB               MVI     A,187               ; WITH CLOCK FREQ OF 375 HZ
0033 D31C               OUT     TIMLOBYT
0035 3EC3               MVI     A,1100$0011B
0037 D318               OUT     CMDSTRG             ; START TIMER
0039 C33F00             JMP     SETUP1
```

; *RST 7.5* THE PROCESSOR JUMPS HERE (3CH) WHEN THE RST 7.5
; INPUT PIN GOES HIGH. JUMP TO INTERRUPT SUBROUTINE.

```
003C                    ORG     START+3CH
003C C38D03             JMP     TIMEOUT 003F 3E1B      SETUP1:  MVI     A,0001$1011B        ; RESET & UNMASK
0041 30                 DB      30H                 ; RST 7.5 WITH 8085 SIM
0042 212518             LXI     H,AVGTABLE          ; POINT TO START OF AVG STORAGE
0045 222118             SHLD    SAVPNTR
0048 20                 DB      20H                 ; GET SID IN A (8085 RIM)
0049 E680               ANI     1000$0000B          ; MASK FOR B-7
004B FE80               CPI     1000$0000B          ; B-7 = 1 FOR A TO D INPUT
004D CA5500             JZ      SETUP2              ; B-7 = 0 FOR BUS INPUT
0050 3EFF               MVI     A,0FFH              ; MUST BE 0 SO SET
0052 321118             STA     BUSFLG              ; BUS FLAG
0055 FB       SETUP2:   EI                          ; ENABLE SYSTEM INTERRUPTS
```

; MAIN IS THE MAIN SYSTEM CONTROL ROUTINE

```
0056 3E0A      MAIN:    MVI     A,10                ; WATCHDOG CYCLE COUNTER TO BE
0058 321718             STA     WATCHFLG            ; DECREMENTED BY TIMER INTERRUPT
005B AF                 XRA     A                   ; ZERO A
005C 320E18             STA     AVGFLG              ; SET TO MAIN DISPLAY
005F DBC0               IN      CNTRLPT             ; SET UP NORMAL DP DISPLAY
0061 E6EF               ANI     1110$1111B          ; TURN ON MID DP (B4 LO)
0063 F628               ORI     0010$1000B          ; TURN OFF END DP'S (B3&B5 HI)
0065 D3C0               OUT     CNTRLPT
0067 CDB203    MAIN1:   CALL    READSWS
006A 3A0618             LDA     INPUTFLG
006D FE00               CPI     0
006F C2AB00             JNZ     SHOWINS
0072 3A0418             LDA     TRIPFLG
0075 FE00               CPI     0
0077 C21301             JNZ     SHOWTRP
007A 3A0518             LDA     SLEEPFLG
007D FE00               CPI     0
007F C25D01             JNZ     SHOWPR
0082 3A0118             LDA     LSDFLG
0085 FE00               CPI     0
0087 C2E900             JNZ     SHOWPWR
008A 3A0218             LDA     MIDFLG
008D FE00               CPI     0
008F C2FA00             JNZ     SHOWREF
0092 3A0318             LDA     MSDFLG
0095 FE00               CPI     0
```

```
0097 C20201            JNZ      SHOW8
009A 3A1018            LDA      GOFLG        ; SEE IF INPUTS HAVE BEEN
009D FE00              CPI      0            ; READ YET
009F CA5600            JZ       MAIN         ; NO, DON'T DISPLAY TILL IT HAS!
00A2 CD2002            CALL     UPDATE
00A5 CDC002            CALL     CKALARM
00A8 C35600            JMP      MAIN

; SHOW ROUTINES DISPLAY SELECTED MAINTENANCE AND CHECKING
            ; INFORMATION AS APPROPRIATE PANEL BUTTONS ARE PRESSED.

00AB 3EFF     SHOWINS: MVI      A,0FFH
00AD 321018            STA      GOFLG        ; ENABLE SYSTEM OPERATION
00B0 DB00              IN       CNTRLPT
00B2 E6F7              ANI      1111$0111B   ; TURN ON RT DP (B3 LO)
00B4 F630              ORI      0011$0000B   ; TURN OFF OTHER DP'S (B4&5 HI)
00B6 D300              OUT      CNTRLPT      ; (TO SOUND BEEPER FOR TEST SET B2 HI)
00B8 3A1118            LDA      BUSFLG       ; GET BUS INPUT FLAG
00BB FE00              CPI      0            ; IF NOT SET,
00BD CAD700            JZ       SHOWATOD     ; SHOW A TO D INPUTS
            SHOWBUS:
00C0 CD9104            CALL     GETBUS       ; GET BUS INPUTS IN DE
00C3 42                MOV      B,D          ; SAVE HEART RATE IN B
00C4 1600              MVI      D,0          ; CLEAR D
00C6 CDB001            CALL     SECHAN1      ; GO DISPLY SYSTOLIC PRES IN E
00C9 3EFF              MVI      A,0FFH       ; SET FLAG TO ENABLE
00CB 320E18            STA      AVGFLG       ; SECOND DISPLAY
00CE 58                MOV      E,B          ; GET HEART RATE IN E
00CF 1600              MVI      D,0          ; CLEAR D
00D1 CDB001            CALL     SECHAN1      ; GO DISPLAY HEART RATE IN E
00D4 C35600            JMP      MAIN
            SHOWATOD:
00D7 3E02              MVI      A,2          ; SELECT SYSTOLIC PRES.
00D9 CDAA01            CALL     SECHAN
00DC 3EFF              MVI      A,0FFH       ; SET FLAG TO ENABLE
00DE 320E18            STA      AVGFLG       ; SECOND DISPLAY
00E1 3E01              MVI      A,1          ; SELECT HEART RATE
00E3 CDAA01            CALL     SECHAN
00E6 C35600            JMP      MAIN

00E9 3E06     SHOWPWR: MVI      A,6          ; SELECT VCC/2 CHANNEL
00EB CD0D04            CALL     ATOD
00EE 1602              MVI      D,2
00F0 5F                MOV      E,A          ; PUT VOLTAGE IN E
00F1 CD1E05            CALL     MULTDE       ; MULTIPLY VCC/2 * 2
00F4 CDB001            CALL     SECHAN1      ; SHOW BCD VALUE (MAX 510)
00F7 C36700            JMP      MAIN1

00FA 3E07     SHOWREF: MVI      A,7          ; SELECT VREF CHANNEL
00FC CDAA01            CALL     SECHAN       ; SHOW BCD VALUE (APPRX 250)
00FF C36700            JMP      MAIN1

0102 117803   SHOW8:   LXI      D,888        ; PUT 888 IN DISPLAY
0105 CDB001            CALL     SECHAN1
0108 3EFF              MVI      A,0FFH
010A 320E18            STA      AVGFLG       ; TURN ON AVG DISPLAY
010D CDB001            CALL     SECHAN1
0110 C35600            JMP      MAIN         ; TO CHECK LED SEGMENTS 0113 2A1D18   SHOWTRP: LHLD     TRIP         ; GET CURRENT TRIP POINT
0116 EB                XCHG                  ; PUT IT IN DE
0117 CDBD01            CALL     SECHAN2      ; SHOW CURRENT TRIP POINT
011A 2A1D18            LHLD     TRIP         ; GET CURRENT TRIP POINT IN HL
011D 3A0118            LDA      LSDFLG
0120 FE00              CPI      0
0122 C24201            JNZ      SLSD
```

```
0125 3A0218          LDA     MIDFLG
0128 FE00            CPI     0
012A C24B01          JNZ     SMID
012D 3A0318          LDA     MSDFLG
0130 FE00            CPI     0
0132 C25401          JNZ     SMSD

0135 AF      TOGLFLG:XRA     A
0136 320A18          STA     LSDSFLG
0139 320B18          STA     MIDSFLG
013C 320C18          STA     MSDSFLG
013F C36700          JMP     MAIN1

0142 CD1803  SLSD:   CALL    SETLSD          ; INCREMENT DIGIT
0145 221D18          SHLD    TRIP            ; SAVE UPDATED TRIP POINT
0148 C36700          JMP     MAIN1
014B CD4403  SMID:   CALL    SETMID
014E 221D18          SHLD    TRIP
0151 C36700          JMP     MAIN1
0154 CD7003  SMSD:   CALL    SETMSD
0157 221D18          SHLD    TRIP
015A C36700          JMP     MAIN1

015D 3EFF    SHOWPR: MVI     A,0FFH          ; SET ALARM SILENCE FLAG
015F 320818          STA     OFONFLG
0162 DB00            IN      CNTRLPT
0164 E6F7            ANI     1111$0111B      ; TURN ON RT DP (B3 LO)
0166 F630            ORI     0011$0000B      ; TURN OFF OTHER DP'S (B4&5 HI)
0168 D300            OUT     CNTRLPT
016A 2A2318          LHLD    PRSAVE          ; GET CURRENT MDI PRESSURE
016D EB              XCHG
016E CDBD01          CALL    SECHAN2
0171 2A2318          LHLD    PRSAVE
0174 3A0118          LDA     LSDFLG
0177 FE00            CPI     0
0179 C28F01          JNZ     PLSD
017C 3A0218          LDA     MIDFLG
017F FE00            CPI     0
0181 C29801          JNZ     PMID
0184 3A0318          LDA     MSDFLG
0187 FE00            CPI     0
0189 C2A101          JNZ     PMSD
018C C33501          JMP     TOGLFLG

018F CD1803  PLSD:   CALL    SETLSD
0192 222318          SHLD    PRSAVE
0195 C36700          JMP     MAIN1
0198 CD4403  PMID:   CALL    SETMID
019B 222318          SHLD    PRSAVE
019E C36700          JMP     MAIN1
01A1 CD7003  PMSD:   CALL    SETMSD
01A4 222318          SHLD    PRSAVE
01A7 C36700          JMP     MAIN1

01AA CD0D04  SECHAN: CALL    ATOD
01AD 1600            MVI     D,0             ; CLEAR D
01AF 5F              MOV     E,A             ; PUT HEX VALUE IN E
01B0 DB00    SECHAN1:IN      CNTRLPT
01B2 F601            ORI     0000$0001B
01B4 D300            OUT     CNTRLPT         ; TURN ON DISPLAY
01B6 CD4805          CALL    BINBCD          ; CONVERT HEX TO BCD
01B9 CD8205          CALL    SHOWLSD         ; SHOW BCD VALUE (MAX 255)
01BC C9              RET

01BD DB00    SECHAN2:IN      CNTRLPT
01BF F601            ORI     0000$0001B
```

```
01C1 D300              OUT      CNTRLPT
01C3 CD4805            CALL     BINBCD
01C6 CD9905            CALL     SHOWMSD       ; SHOW BCD VALUE (MAX 99,9XX)
01C9 C9                RET

; MULTRXP PRODUCES THE PRODUCT OF A TO D CHANNELS
                ; #1, & #2 OR INPUT FROM THE DATA BUS WHEN CONNECTED,
                ; AND SAVES THE RESULT IN RAM AT "PSAVE".
                ; IF THE PRODUCT EXCEEDS THE TRIP POINT, THE ALARM
                ; FLAG "ALMFLG" WILL BE SET. A RATE LESS THAN 35
                ; WILL BE IGNORED WITH NO PRODUCT UPDATE PERFORMED.
                ; A PRESSURE LESS THAN 35 CAUSES MANUALLY PRESET INNITAL PRESSURE
                ; TO BE USED UNTIL A MONITORED 35 OR GREATER PRESSURE IS DETECTED.
                ; DESTROYS A,PSW,D,& E

01CA 3A1118     MULTRXP:LDA      BUSFLG        ; GET BUS INPUT FLAG
01CD FE00              CPI      0             ; IF NOT SET, MULTIPLY
01CF CAD801            JZ       MULTAD        ; A TO D INPUTS

01D2 CD9104     MULTBUS:CALL     GETBUS        ; GET BUS INPUT IN DE
01D5 C3E401            JMP      PROCESS

01D8 3E01       MULTAD: MVI      A,1           ; SELECT HEART RATE
01DA CD0D04            CALL     ATOD          ; GET VALUE
01DD 57                MOV      D,A           ; PUT HEART RATE IN D
01DE 3E02              MVI      A,2           ; SELECT BLOOD PRES.
01E0 CD0D04            CALL     ATOD
01E3 5F                MOV      E,A           ; PUT BLOOD PRES. IN E

01E4 7A         PROCESS:MOV      A,D           ; PUT HEART RATE IN A
01E5 FE23              CPI      35            ; IS IT OVER 35?
01E7 D8                RC                     ; NO, RETURN WITHOUT UPDATING
01E8 7B                MOV      A,E           ; PUT SYSTOLIC PRES IN A
01E9 FE23              CPI      35            ; IS IT OVER 35?
01EB D2F701            JNC      PRESOK        ; YES, GO PROCESS IT
01EE 2A2318            LHLD     PRSAVE        ; NO, GET MDI PRES
01F1 3E64              MVI      A,100         ; DIVIDE 16 BIT PRESSURE
01F3 CD3605            CALL     DIVIDE        ; BY 100 TO MAKE 8 BIT
01F6 5D                MOV      E,L           ; PUT QUOTENT IN E

01F7 CD1E05     PRESOK: CALL     MULTDE        ; MULTIPLY D * E
01FA EB                XCHG
01FB 221F18            SHLD     PSAVE         ; SAVE CURRENT PRODUCT
01FE EB                XCHG
01FF 2A1D18            LHLD     TRIP          ; GET TRIP VALUE IN HL
0202 7C                MOV      A,H
0203 BA                CMP      D             ; IS HI BYTE = OR GREATER?
0204 DA0F02            JC       OVER
0207 CA1502            JZ       CKLOBYT

020A AF         OK:     XRA      A
020B 320918            STA      ALMFLG        ; UN-SET ALARM FLAG
020E C9                RET 020F 3EFF       OVER:   MVI      A,0FFH
0211 320918            STA      ALMFLG        ; SET ALARM FLAG
0214 C9                RET 0215 7D         CKLOBYT:MOV      A,L
0216 BB                CMP      E             ; IS LO BYTE = OR GREATER?
0217 DA0F02            JC       OVER
021A CA0F02            JZ       OVER
021D C30A02            JMP      OK

; UPDATE INNITIATES A NEW PULSE-PRESSURE PRODUCT
                ; ONCE EACH SECOND AND INNITIATES AN AVERAGE ONCE
```

```
                                ; EACH 10 SECONDS.
                                ; DESTROYS A,PSW,D,& E 0220 3A0D18      UPDATE: LDA    MULTFLG
0223 FE00                CPI    0
0225 C8                  RZ                     ; IF ALREADY DONE, RETURN
0226 AF                  XRA    A
0227 320D18              STA    MULTFLG         ; IF NOT, DON'T DO AGAIN
022A CDCA01              CALL   MULTRXP         ; GO GET NEW PRODUCT
022D 3A1518              LDA    SECCOUNT        ; GET # OF SECONDS SINCE LAST TIME
0230 3C                  INR    A               ; ADD ONE SECOND
0231 FE0A                CPI    10              ; IS IT 10 SECONDS YET?
0233 CA3A02              JZ     UPDATE1
0236 321518              STA    SECCOUNT        ; NO, SAVE NEW COUNT
0239 C9                  RET
                 UPDATE1:
023A AF                  XRA    A
023B 321518              STA    SECCOUNT        ; ZERO SECONDS COUNTER
023E CD4202              CALL   AVERAGE         ; GO COMPUTE AVERAGE
0241 C9                  RET

; AVERAGE KEEPS THE MOST SIGNIFICANT DIGITS OF THE CURRENT
                                ; PRODUCT EACH 10 SECONDS AND CALCULATES THE AVERAGE ON A
                                ; TRAVELING TWO MINUTE WINDOW. ZEROS ARE DISPLAYED FOR
                                ; THE FIRST TWO MINUTES.

0242 3A0F18      AVERAGE:LDA    STARTFLG        ; SEE IF 1'ST 2 MIN ARE UP YET
0245 FE00                CPI    0
0247 CA7302              JZ     NOTYET
024A AF                  XRA    A
024B 321318              STA    AVGCNT2         ; ZERO THE SECOND LIST COUNTER
024E 112518              LXI    D,AVGTABLE      ; PUT AVG TABLE ST PT IN DE
0251 210000              LXI    H,0             ; CLEAR HL & BC
0254 010000              LXI    B,0
0257 1A          DOALL12:LDAX   D               ; GET VALUE TO AVERAGE
0258 4F                  MOV    C,A             ; PUT VALUE IN C OF BC
0259 09                  DAD    B               ; ADD BC TO HL (SUM IN HL)
025A 13                  INX    D               ; NEXT VALUE
025B 3A1318              LDA    AVGCNT2         ; SEE IF 12 ARE DONE YET
025E 3C                  INR    A
025F 321318              STA    AVGCNT2         ; UPDATE LIST COUNTER
0262 FE0C                CPI    12
0264 C25702              JNZ    DOALL12         ; IF NOT, DO THEM 0267 3E0C                MVI    A,12            ; HERE IS WHERE WE COMPUTE
0269 CD3605              CALL   DIVIDE          ; THE AVERAGE OF 12 PRODUCTS
026C 7D                  MOV    A,L             ; SAVED EACH 10 SECONDS
026D 321418              STA    AVGSAVE         ; STORE THE AVERAGE
0270 C37F02              JMP    SAVDATA 0273 3A1618      NOTYET: LDA    STARTCNT        ; HERE WE SAVE THE FIRST 12
0276 3C                  INR    A               ; PRODUCT VALUES BEFORE ALLOWING
0277 FE0B                CPI    11              ; THE FIRST AVG CALC ON POWER-UP
0279 CABA02              JZ     SETSTART        ; GO SET THE START FLAG
027C 321618              STA    STARTCNT        ; NOT 11 YET, SAVE COUNT & CONTINUE

SAVDATA:
027F 2A1F18              LHLD   PSAVE           ; GET CURRENT PRODUCT
0282 3E64                MVI    A,100           ; LOP OFF 10'S DIGITS
0284 CD3605              CALL   DIVIDE
0287 7D                  MOV    A,L             ; PUT LOPPED OFF VALUE IN A
0288 2A2118              LHLD   SAVPNTR         ; GET TABLE PNTR IN HL
028B 77                  MOV    M,A             ; PUT LOPPED OFF VALUE IN TABLE
028C 23                  INX    H               ; NEXT TABLE LOC
028D 3A1218              LDA    AVGCNT1         ; ARE WE TO TABLE TOP YET?
0290 3C                  INR    A
```

```
0291 321218              STA     AVGCNT1        ; UPDATE LIST COUNTER
0294 FE0C                CPI     12             ; ARE ALL 12 DONE YET?
0296 CA9F02              JZ      RSTPNTR        ; IF SO, GO RESET POINTER TO BEGINNING
0299 222118              SHLD    SAVPNTR        ; NO, SAVE CURRENT POINTER
029C C3A902              JMP     SHOWAVG

RSTPNTR:                          ; CIRCULATE TABLE POINTER TO KEEP UPDATING OLDEST ENTRY
029F 212518              LXI     H,AVGTABLE     ; BEGINNING OF AVG VALUE TABLE
02A2 222118              SHLD    SAVPNTR
02A5 AF                  XRA     A
02A6 321218              STA     AVGCNT1        ; RE-ZERO FIRST LIST COUNTER
              SHOWAVG:
02A9 3EFF                MVI     A,0FFH         ; SET DISPLAY TO SMALL DIGITS
02AB 320E18              STA     AVGFLG
02AE 2A1418              LHLD    AVGSAVE        ; GET CURRENT AVERAGE
02B1 EB                  XCHG                   ; PUT IT IN DE
02B2 CDB001              CALL    SECHAN1        ; GO SHOW IT
02B5 AF                  XRA     A
02B6 320E18              STA     AVGFLG         ; SET DISPLAY BACK TO LARGE DIGITS
02B9 C9                  RET

SETSTART:
02BA 320F18              STA     STARTFLG       ; SET THE START FLAG
02BD C37F02              JMP     SAVDATA

; CKALARM DISPLAYS CURRENT PRODUCT AND INVOKES
              ; THE ALARM CONDITION IF NECESSARY.
              ; CKBLINK UPDATES BLINK STATUS WITHOUT DISPLAYING.
              ; DESTROYS A,PSW,DE,& HL

02C0 2A1F18   CKALARM:LHLD       PSAVE          ; GET CURRENT PRODUCT
02C3 EB                  XCHG                   ; PUT PRODUCT IN DE
02C4 CD4805              CALL    BINBCD         ; CONVERT TO BCD
02C7 CD9905              CALL    SHOWMSD        ; SHOW BCD VALUE
02CA 3A0918   CKBLINK:LDA        ALMFLG
02CD FE00                CPI     0              ; IF FLAG NOT SET,
02CF CAD602              JZ      RSTALM         ; TURN OFF ALARM
02D2 CDE302              CALL    ALARM          ; OTHERWISE, SET OFF ALARM
02D5 C9                  RET

02D6 DB00     RSTALM: IN         CNTRLPT
02D8 E6FB                ANI     1111$1011B
02DA F601                ORI     0000$0001B
02DC D300                OUT     CNTRLPT        ; TURN OFF ALARM
02DE AF                  XRA     A
02DF 320818              STA     OFONFLG        ; UN-SET ALARM SILENCE FLAG
02E2 C9                  RET

; ALARM IS CALLED WHEN THE ALARM FLAG IS SET BY THE
              ; "MULTRXP" PROGRAM, AND THEN DISCOVERED BY THE "CKALARM"
              ; PROGRAM. THE BEEPER MAY THEN BE SILENCED BY PUSHBUTTON
              ; UNTIL THE ALARM FLAG IS RESET BY FALLING BELOW TRIP POINT
              ; THE ALARM IS SUBSEQUENTLY RESET BY "CKALARM".
              ; DESTROYS A,& PSW

02E3 3A0818   ALARM:  LDA        OFONFLG        ; GET OFF/ON FLAG
02E6 FE00                CPI     0
02E8 C2FC02              JNZ     QUIET
02EB 3A0718              LDA     BLNKFLG
02EE FE00                CPI     0              ; WHEN DISPLAY IS ON,
02F0 CAFC02              JZ      QUIET          ; BEEPER IS OFF
02F3 DB00                IN      CNTRLPT
02F5 F604                ORI     0000$0100B
02F7 D300                OUT     CNTRLPT        ; TURN ON BEEPER
02F9 C30203              JMP     BLINK
02FC DB00     QUIET:  IN         CNTRLPT
```

```
02FE E6FB              ANI     1111$1011B
0300 D300              OUT     CNTRLPT       ; TURN OFF BEEPER
0302 3A0718   BLINK:   LDA     BLNKFLG       ; GET BLINK FLAG
0305 FE00              CPI     0
0307 C21103            JNZ     BLANK
030A DB00              IN      CNTRLPT
030C F601              ORI     0000$0001B
030E D300              OUT     CNTRLPT       ; TURN ON DISPLAY
0310 C9                RET

0311 DB00     BLANK:   IN      CNTRLPT
0313 E6FE              ANI     1111$1110B
0315 D300              OUT     CNTRLPT       ; TURN OFF DISPLAY
0317 C9                RET

; SETXXX ARE ROUTINES TO SET THE THREE HIGH ORDER DIGITS
              ; OF THE DISPLAYED 16 BIT VALUE. THEY EACH INCREMENT THEIR
              ; APPROPRIATE DIGIT ONCE FOR EACH PRESS OF THE DIGIT BUTTON.
              ; CALL WITH THE CURRENT DISPLAYED VALUE IN HL.
              ; THE NEW VALUE IS RETURNED IN HL.
              ; DESTROYS ALL REGISTERS 0318 3A0A18   SETLSD:  LDA     LSDSFLG       ; SEE IF ALREADY INCREMENTED
031B FE00              CPI     0
031D C0                RNZ                   ; IF SO, RETURN
031E 2F                CMA
031F 320A18            STA     LSDSFLG       ; IF NOT, SET FLAG
0322 CDD605            CALL    DEBOUNCE      ; DEBOUNCE THE BUTTON
0325 EB                XCHG                  ; PUT TRIP PT IN DE
0326 CD4805            CALL    BINBCD        ; CONVERT IT TO BCD
0329 3A1918            LDA     BCDSAVE+1     ; GET THE 1,000'S DIGIT
032C 47                MOV     B,A           ; SAVE IT IN B
032D EB                XCHG                  ; PUT TRIP PT BACK IN HL
032E 116400            LXI     D,100         ; LOAD INCREMENT VALUE IN DE
0331 19                DAD     D             ; ADD IT TO HL
0332 EB                XCHG                  ; PUT TRIP PT + 100 IN DE
0333 CD4805            CALL    BINBCD        ; CONVERT IT TO BCD
0336 EB                XCHG                  ; PUT IT BACK IN HL
0337 3A1918            LDA     BCDSAVE+1     ; GET NEW 1,000'S DIGIT
033A B8                CMP     B             ; SEE IF DIFFERENT FROM OLD
033B C23FC3            JNZ     SUB1K         ; IF SO, GO SUBTRACT 1,000
033E C9                RET                   ; IF NOT, RET WITH NEW TRIP PT IN HL 033F 1118FC   SUB1K:   LXI     D,0FC18H      ; 64536 ADDED TO TRIP PT WILL
0342 19                DAD     D             ; OVERFLOW 16-BITS & EFFECTIVLY
0343 C9                RET                   ; SUBTRACT 1,000

0344 3A0B18   SETMID:  LDA     MIDSFLG       ; THIS ROUTINE IS VERY SIMILAR
0347 FE00              CPI     0             ; TO THE PRECEEDING ONE
0349 C0                RNZ
034A 2F                CMA
034B 320B18            STA     MIDSFLG
034E CDD605            CALL    DEBOUNCE
0351 EB                XCHG
0352 CD4805            CALL    BINBCD
0355 3A1818            LDA     BCDSAVE       ; GET 10,000'S DIGIT
0358 47                MOV     B,A
0359 EB                XCHG
035A 11E803            LXI     D,1000        ; ADD 1000 TO INCREMENT
035D 19                DAD     D             ; THE 1,000'S DIGIT
035E EB                XCHG
035F CD4805            CALL    BINBCD
0362 EB                XCHG
0363 3A1818            LDA     BCDSAVE       ; GET NEW 10,000'S DIGIT
0366 B8                CMP     B             ; IF 10,000'S DIGIT HAS CHANGED
0367 C26B03            JNZ     SUB10K        ; GO SUBTRACT 10,000 FROM TRIP PT
```

```
036A C9                 RET 036B 11F0D8    SUB10K:  LXI     D,0D8F0H        ; 55536
036E 19                 DAD     D
036F C9                 RET 0370 3A0C18    SETMSD:  LDA     MSDSFLG         ; THIS ROUTINE IS ALSO
0373 FE00               CPI     0               ; SIMILAR TO ABOVE
0375 C0                 RNZ
0376 2F                 CMA
0377 320C18             STA     MSDSFLG
037A CDD605             CALL    DEBOUNCE
037D 111027             LXI     D,10000
0380 19                 DAD     D
0381 7C                 MOV     A,H
0382 FEC3               CPI     0C3H            ; DON'T ALLOW MSD
0384 D28803             JNC     SUB50K          ; TO INCREMENT PAST 4
0387 C9                 RET 0388 11B03C    SUB50K:  LXI     D,3CB0H         ; 15536
038B 19                 DAD     D
038C C9                 RET

; TIMEOUT IS ENTERED ONLY BY A JUMP FROM RST 7.5 ONCE EACH 1/2 SECOND

038D F5        TIMEOUT: PUSH    PSW             ; SAVE REGISTERS
038E 3A1718             LDA     WATCHFLG        ; GET WATCHDOG FLAG
0391 3D                 DCR     A               ; SUBTRACT 1
0392 CAAB03             JZ      ERROR           ; IF 0, SYSTEM MUST BE "HUNGUP"
0395 321718             STA     WATCHFLG        ; IF NOT, SAVE DECR NUMBER
0398 3A0718             LDA     BLNKFLG         ; & CONTINUE ON
039B 2F                 CMA                     ; IF 0, SET TO FF
039C 320718             STA     BLNKFLG         ; IF NOT, SET TO 0
039F 320D18             STA     MULTFLG         ; ALSO FLIP-FLOP MULTIPLY FLAG
03A2 CDCA02             CALL    CKBLINK         ; BE SURE BLINK STATUS IS UPDATED

03A5 3E10     RESET75:  MVI     A,0001$0000B
                        SIM                     ; 8085 SIM INSTRUCTION
03A7+30                 DB      30H
03A8 F1                 POP     PSW             ; RESTORE REGISTERS
03A9 FB                 EI                      ; RE-ENABLE INTERRUPTS
03AA C9                 RET

03AB 31FF18    ERROR:   LXI     SP,RAMTOP       ; COME HERE TO ATTEMPT AN IN CYCLE
03AE FB                 EI                      ; RESTART IF WATCHDOG CYCLE COUNTER
03AF C35600             JMP     MAIN            ; HAS COUNTED TO 0

; READSWS IS A ROUTINE TO READ THE PANEL SWITCHES &
        ; STORE THE APPROPRIATE FLAGS REPRESENTING CURRENT
        ; SWITCH SETTINGS.
        ; DESTROYS A,& PSW

03B2 C5        READSWS: PUSH    B
03B3 CDEB03             CALL    CLRFLGS         ; CLEAR ANY RESIDUAL SWITCH FLAGS
03B6 DB1B              IN      SWPT            ; READ SWITCHES
03B8 2F                 CMA                     ; INVERT THE LOGIC
03B9 47                 MOV     B,A             ; SAVE SWITCH IMAGE IN B
03BA E601               ANI     0000$0001B
03BC FE01               CPI     0000$0001B
03BE CCF503             CZ      LSD
03C1 78                 MOV     A,B
03C2 E602               ANI     0000$0010B
03C4 FE02               CPI     0000$0010B
03C6 CCF903             CZ      MID
03C9 78                 MOV     A,B
03CA E604               ANI     0000$0100B
```

```
03CC FE04              CPI     0000$0100B
03CE CCFD03            CZ      MSD
03D1 78                MOV     A,B
03D2 E608              ANI     0000$1000B
03D4 FE08              CPI     0000$1000B
03D6 CC0104            CZ      SHWTRP
03D9 78                MOV     A,B
03DA E610              ANI     0001$0000B
03DC FE10              CPI     0001$0000B
03DE CC0504            CZ      SILBEP
03E1 78                MOV     A,B
03E2 E620              ANI     0010$0000B
03E4 FE20              CPI     0010$0000B
03E6 CC0904            CZ      INPUTS
03E9 C1                POP     B
03EA C9                RET

; ROUTINE TO CLEAR SWITCH FLAGS

03EB 210618   CLRFLGS:LXI      H,INPUTFLG
03EE AF                XRA     A
03EF 77       CLRFLG: MOV      M,A
03F0 2D                DCR     L               ; WHEN L = 0 (1800H)
03F1 C2EF03            JNZ     CLRFLG          ; EXIT TO CALLER
03F4 C9                RET

; COME HERE TO SET THE SWITCH FLAGS

03F5 320118   LSD:    STA     LSDFLG
03F8 C9               RET
03F9 320218   MID:    STA     MIDFLG
03FC C9               RET
03FD 320318   MSD:    STA     MSDFLG
0400 C9               RET
0401 320418   SHWTRP: STA     TRIPFLG
0404 C9               RET
0405 320518   SILBEP: STA     SLBEPFLG
0408 C9               RET
0409 320618   INPUTS: STA     INPUTFLG
040C C9               RET

; ATOD IS A ROUTINE TO CONVERT ANALOG VOLTAGE LEVELS
              ; FROM ONE OF SIX CHANNELS (1 - 6) AS SPECIFIED IN THE
              ; A REG. AN 8-BIT VALUE REPRESENTING THE VOLTAGE IS
              ; RETURNED A.
              ; ZERO IS RETURNED WHEN LESS THAN 20 MV IS DETECTED.
              ; DESTROYS A,& PSW

040D C5       ATOD:   PUSH    B               ; SAVE REGISTERS
040E E5               PUSH    H
040F 4F               MOV     C,A             ; PUT CHANNEL # IN C
0410 CD1A04           CALL    CNVRSN          ; GET RAW ANALOG VALUE
0413 CD6104           CALL    ADJUST          ; COMPENSATE SCALE
0416 79               MOV     A,C             ; PUT HEX VOLTAGE IN A
0417 E1               POP     H
0418 C1               POP     B               ; RESTORE REGISTERS
0419 C9               RET

041A AF       CNVRSN: XRA     A
041B 320018           STA     OVFLFLG         ; ZERO OVERFLOW FLAG
041E 79               MOV     A,C             ; GET CHANNEL #
041F 17               RAL                     ; & ROTATE TO
0420 17               RAL                     ; UPPER 4-BITS
0421 17               RAL                     ; THEN MASK OFF
0422 17               RAL                     ; ALL BUT B4,5&6
0423 E670             ANI     0111$0000B
0425 4F               MOV     C,A             ; SAVE IN C
```

```
0426 DB1A                IN     MSDPT            ; MASK OFF OLD CONTROL BITS
0428 E60F                ANI    0000$1111B       ; BITS 0 - 3
042A B1                  ORA    C                ; MERGE WITH OLD DIGIT
042B D31A                OUT    MSDPT            ; SEND CHANNEL ADDRESS
042D CDD605              CALL   DEBOUNCE         ; CHARGE RAMP CAPACITOR
0430 F3                  DI                      ; DISABLE INTERRUPTS DURING COUNT
0431 0E00                MVI    C,0              ; ZERO COUNTER
0433 F680                ORI    1000$0000B       ; BIT 7 = 1
0435 D31A                OUT    MSDPT            ; START CONVERSION
0437 0C        COUNT:    INR    C                ; LOOP HERE UNTIL TRAPPED
0438 C23704              JNZ    COUNT            ; OR UNTIL OVERFLOWED
043B 320018    TILTRAP:  STA    OVFLFLG          ; SET OVERFLOW FLAG
043E C33B04              JMP    TILTRAP          ; & WAIT FOR TRAP INTERRUPT

; TRAPPED IS ENTERED ONLY BY A JUMP FROM THE "TRAP"
; INTERRUPT VECTOR.

TRAPPED:
0441 F1                  POP    PSW              ; RESTORE STACK
0442 FB                  EI                      ; RE-ENABLE INTERRUPTS
0443 DB1A                IN     MSDPT            ; READ PORT
0445 E60F                ANI    0000$1111B       ; BITS 0 - 3
0447 D31A                OUT    MSDPT            ; TURN OFF A TO D CHIP
0449 3A0018              LDA    OVFLFLG          ; SEE IF TRAPPED AFTER
044C FE00                CPI    0                ; AN OVERFLOW
044E C25904              JNZ    OVFLOW           ; IF SO, REMEDY IT
0451 DB00                IN     CNTRLPT          ; IF NOT, BE SURE THAT
0453 F638                ORI    0011$1000B       ; BITS 3,4&5 = 1
0455 D300                OUT    CNTRLPT          ; DECIMAL PTS ARE OFF
0457 A7                  ANA    A                ; TURN OFF CARRY FLAG
0458 C9                  RET                     ; & RETURN

0459 DB00      OVFLOW:   IN     CNTRLPT          ; TURN ON ALL 3 DP'S
045B E6C7                ANI    1100$0111B       ; BITS 3,4&5 = 0
045D D300                OUT    CNTRLPT
045F 37                  STC                     ; SET CARRY FLAG
0460 C9                  RET                     ; & RETURN

; ADJUST COMPENSATES THE A TO D INPUT VALUE TO ALLOW
; FOR RANGE NONLINEARITY.

0461 79        ADJUST:   MOV    A,C              ; PUT COUNT IN A
0462 FE14                CPI    20               ; SEE IF LESS THAN 20
0464 DA7704              JC     ZERO             ; IF SO, MAKE 0

0467 0600                MVI    B,0
0469 217E04              LXI    H,TABLE
046C A7        LOOKUP:   ANA    A                ; CLEAR CY FLAG
046D 7E                  MOV    A,M              ; GET VALUE FROM TABLE
046E 91                  SUB    C                ; SEE IF VOLTAGE IS LARGER
046F DA7A04              JC     FIX              ; IF SO, GO SUBTRACT # OF
0472 23                  INX    H                ; ACCESSES TO TABLE (B)
0473 04                  INR    B                ; ADD 1 TO B
0474 C36C04              JMP    LOOKUP           ; GO LOOK AGAIN 0477 0E00      ZERO:     MVI    C,0
0479 C9                  RET 047A 79        FIX:      MOV    A,C              ; GET VOLTAGE IN A
047B 90                  SUB    B                ; SUBTRACT # OF TABLE TRYS
047C 4F                  MOV    C,A              ; PUT COMPENSATED VAL IN C
047D C9                  RET

047E E1        TABLE:    DB     225
047F C8                  DB     200
0480 AF                  DB     175
```

```
0481 96              DB      150
0482 7D              DB      125
0483 73              DB      115
0484 69              DB      105
0485 5F              DB       95
0486 55              DB       85
0487 4B              DB       75
0488 46              DB       70
0489 41              DB       65
048A 37              DB       55
048B 2D              DB       45
048C 23              DB       35
048D 19              DB       25
048E 16              DB       22
048F 14              DB       20
0490 0A              DB       10

; GETBUS CHARACTERS FOR HEART RATE AND SYSTOLIC PRESSURE.
             ; SPACELABS RATE CARDULE MUST BE ADDRESSED #1, PRESSURE #2
             ; RETURNS BINARY VALUE FOR RATE IN D AND PRESSURE IN E.
             ; BUS DIGITS MAY HAVE INDEXED DURING READ CYCLE....RE-READ
             ; TO VERIFY DIGITS.
             ; DESTROYS PSW & A

0491 E5      GETBUS: PUSH    H
0492 CDA604          CALL    GETBUSN     ; GET DIGITS IN DE
0495 EB              XCHG                ; SAVE IN HL
0496 CDA604  REDIGIT:CALL    GETBUSN     ; GET DIGITS AGAIN
0499 EB              XCHG                ; NOW HL = NEW, DE = OLD
049A 7A              MOV     A,D         ; GET OLD RATE IN A
049B BC              CMP     H           ; IS IT = TO NEW RATE?
049C C29604          JNZ     REDIGIT     ; NO, TRY AGAIN
049F 7B              MOV     A,E         ; GET OLD PRES. IN A
04A0 BD              CMP     L           ; IS IT = TO NEW PRES.?
04A1 C29604          JNZ     REDIGIT     ; NO, TRY AGAIN
             ; COME HERE IF 2 READS PRODUCE THE SAME DIGITS
04A4 E1              POP     H
04A5 C9              RET                 ; WITH D = RATE & E = PRES.

04A6 C5      GETBUSN:PUSH    B
04A7 0600            MVI     B,0         ; GET HEART RATE DIGITS
04A9 3E66            MVI     A,102       ; FROM SPACELABS BUS
04AB 1664            MVI     D,100       ; GET 100'S DIGIT
04AD CDD804          CALL    GETBUS1
04B0 3E67            MVI     A,103       ; WORD #103
04B2 160A            MVI     D,10        ; GET 10'S DIGIT
04B4 CDD804          CALL    GETBUS1
04B7 3E68            MVI     A,104       ; WORD #104
04B9 CDE304          CALL    BUSDIGIT    ; GET 1'S DIGIT IN A
04BC 80              ADD     B           ; ADD 1'S DIGIT
04BD 4F              MOV     C,A         ; SAVE HEART RATE IN C
04BE 0600            MVI     B,0         ; GET SYSTOLIC PRES DIGITS
04C0 3EA5            MVI     A,165       ; FROM SPACELABS BUS
04C2 1664            MVI     D,100       ; GET 100'S DIGIT
04C4 CDD804          CALL    GETBUS1
04C7 3EA6            MVI     A,166       ; WORD #166
04C9 160A            MVI     D,10        ; GET 10'S DIGIT
04CB CDD804          CALL    GETBUS1
04CE 3EA7            MVI     A,167       ; WORD #167
04D0 CDE304          CALL    BUSDIGIT    ; GET 1'S DIGIT IN A
04D3 80              ADD     B           ; GET 1'S DIGIT
04D4 5F              MOV     E,A         ; SAVE SYSTOLIC PRES IN E
04D5 51              MOV     D,C         ; SAVE HEART RATE IN D
04D6 C1              POP     B
04D7 C9              RET
```

```
04D8 CDE304    GETBUS1:CALL   BUSDIGIT         ; GET DIGIT PER A
04DB 5F                MOV    E,A              ; PUT BCD DIGIT IN E
04DC CD1E05            CALL   MULTDE           ; MULT BY D TO CONVERT
04DF 7B                MOV    A,E              ; TO BINARY & ADD
04E0 80                ADD    B                ; TO VALUE IN B
04E1 47                MOV    B,A              ; SAVE BINARY IN B
04E2 C9                RET

; CALL BUSDIGIT WITH BUS CHARACTER WORD NUMBER IN A.
               ; BCD DIGIT RETURNED IN A.
               ; DESTROYS PSW, A

BUSDIGIT:
04E3 C5                PUSH   B
04E4 4F                MOV    C,A              ; SAVE WORD # IN C
04E5 DB00      REFRAME:IN     CNTRLPT
04E7 F680              ORI    1000$0000B       ; SET DATABUS TO LATCH MODE
04E9 D300              OUT    CNTRLPT          ; (B7 = 1)
04EB 3EFF              MVI    A,1111$1111B     ; SET ALL BITS OF DATABUS
04ED D303              OUT    DATADDR          ; PORT TO OUTPUT
04EF 79                MOV    A,C              ; SET OUTPUT COUNT TO
04F0 D301              OUT    DATAPT           ; WORD # FROM C REG

04F2 DB00      COUNTST:IN     CNTRLPT          ; READ COUNTING LINE TO CATCH
04F4 E640              ANI    0100$0000B       ; LO TO HI TRANSITION (START
04F6 FE40              CPI    0100$0000B       ; OF COUNT)
04F8 C2F204            JNZ    COUNTST          ; IF NOT HI, READ AGAIN
04FB DB00      COUNTSP:IN     CNTRLPT          ; READ COUNTING LINE TO CATCH
04FD E640              ANI    0100$0000B       ; HI TO LO TRANSITION (END
04FF FE40              CPI    0100$0000B       ; OF COUNT)
0501 CAFB04            JZ     COUNTSP          ; IF STILL HI,LOOP TILL LO

0504 AF                XRA    A
0505 D303              OUT    DATADDR          ; SET DATABUS PORT TO INPUT
0507 DB00              IN     CNTRLPT
0509 E67F              ANI    0111$1111B       ; SET DATABUS TO READ MODE
050B D300              OUT    CNTRLPT          ; (B7 = 0)
050D DB01              IN     DATAPT           ; READ BUS LATCH
050F 47                MOV    B,A              ; SAVE BUS IMAGE IN B
0510 E603              ANI    0000$0011B       ; B0 = 1, B1 = 0 FOR CORRECT FRAME
0512 FE01              CPI    0000$0001B       ; NUMBER
0514 C2E504            JNZ    REFRAME          ; NO, GO GET ANOTHER
                                               ; CORRECT FRAME #
0517 78                MOV    A,B              ; NOW DECODE DIGIT
0518 1F                RAR                     ; SHIFT OFF LOWER
0519 1F                RAR                     ; 2-BIT FRAME #
051A E60F              ANI    0000$1111B       ; LOP OFF UPPER 4-BITS
051C C1                POP    B
051D C9                RET                     ; WITH BCD DIGIT IN A

; MULTDE PERFORMS AN 8-BIT BINARY MULTIPLICATION ON THE
               ; UNSIGNED VALUES IN THE D & E REGISTERS AND RETURNS A
               ; 16-BIT PRODUCT IN DE.
               ; DESTROYS A,& PSW

051E C5        MULTDE: PUSH   B                ; SAVE REGISTERS
051F E5                PUSH   H                ; MULTIPLICAND IS IN E
0520 7A                MOV    A,D              ; PUT MULTIPLIER IN A
0521 1600              MVI    D,0              ; EXTEND DE TO 16-BITS
0523 210000            LXI    H,0              ; PRODUCT NOW = 0
0526 0608              MVI    B,8              ; COUNT = 8
0528 29        MULT:   DAD    H                ; PRODUCT = PRODUCT * 2
0529 17                RAL                     ; SHIFT A TO MATCH HL
052A D22E05            JNC    CKCOUNT          ; IS CARRY FROM MULTIPLIER 1?
052D 19                DAD    D                ; YES, PROD. = PROD. + MULTIPLICAND
052E 05        CKCOUNT:DCR    B                ; DECREMENT COUNT
052F C22805            JNZ    MULT
```

```
0532 EB              XCHG              ; PUT PRODUCT IN DE
0533 E1              POP    H
0534 C1              POP    B          ; RESTORE REGISTERS
0535 C9              RET

; DIVIDE DIVIDES THE 16-BIT BINARY NUMBER FOUND IN HL
                ; BY THE 8-BIT DIVISOR FOUND IN A. THE QUOTIENT IS RETURNED
                ; IN L WITH THE REMAINDER IN H.
                ; DESTROYS A, PSW,& HL

0536 C5      DIVIDE: PUSH   B
0537 4F              MOV    C,A
0538 0608            MVI    B,8
053A 29      DIV:    DAD    H
053B 7C              MOV    A,H
053C 91              SUB    C
053D DA4205          JC     CNT
0540 67              MOV    H,A
0541 2C              INR    L
0542 05      CNT:    DCR    B
0543 C23A05          JNZ    DIV
0546 C1              POP    B
0547 C9              RET

; BINBCD RECIEVES A BINARY NUMBER IN THE DE REGISTER PAIR
                ; & CONVERTS IT TO AS MANY AS 5 BCD DIGITS STORING THEM
                ; STARTING WITH THE MOST SIGNIFICANT DIGIT AT "BCDSAVE".
                ; ONE DIGIT IS STORED PER BYTE. AN OPTIONAL ASCII VERSION
                ; FOR THE DIGITS IS ENABLED BY CHANGING A CONSTANT AS NOTED.
                ; DESTROYS NOTHING

0548 F5      BINBCD: PUSH   PSW        ; SAVE ALL REGISTERS
0549 C5              PUSH   B
054A D5              PUSH   D
054B E5              PUSH   H
054C 211818          LXI    H,BCDSAVE  ; POINT TO START OF STORAGE
054F EB              XCHG
0550 01F0D8          LXI    B,0D8F0H   ; 10,000'S DIGIT CONSTANT
0553 CD7105          CALL   DECNO
0556 0118FC          LXI    B,0FC18H   ; 1,000'S DIGIT CONSTANT
0559 CD7105          CALL   DECNO
055C 019CFF          LXI    B,0FF9CH   ; 100'S DIGIT CONSTANT
055F CD7105          CALL   DECNO
0562 01F6FF          LXI    B,0FFF6H   ; 10'S DIGIT CONSTANT
0565 CD7105          CALL   DECNO
0568 7D              MOV    A,L
0569 C600            ADI    0          ; (E0H IF ASCII CODE DESIRED)
056B 12              STAX   D          ; STORE 1'S DIGIT
056C E1              POP    H
056D D1              POP    D
056E C1              POP    B
056F F1              POP    PSW        ; RESTORE REGISTERS
0570 C9              RET 0571 3E00     DECNO: MVI    A,0        ; (B0H IF ASCII CODE DESIRED)
0573 D5              PUSH   D
0574 5D      MORE:   MOV    E,L        ; CIRCULATE HERE UNTIL
0575 54              MOV    D,H        ; CARRY FLAG IS CLEARED
0576 3C              INR    A          ; AFTER ADDING THE "B"
0577 09              DAD    B          ; CONSTANT N TIMES
0578 DA7405          JC     MORE
057B 3D              DCR    A
057C 6B              MOV    L,E
057D 62              MOV    H,D
057E D1              POP    D
057F 12              STAX   D          ; STORE THE CONVERTED DIGIT
```

```
0580 13            INX      D                  ; INCR. D TO NEXT DIGIT POS.
0581 C9            RET

; SHOWMSD & SHOWLSD GET THE BCD DIGITS FROM MEMORY
                   ; AS CREATED BY "BINBCD" AND DISPLAY THE THREE HIGHEST
                   ; OR THREE LOWEST DIGITS RESPECTFULLY.
                   ; DESTROY A,& PSW

0582 D5    SHOWLSD:PUSH     D
0583 3A1C18        LDA      BCDSAVE+4          ; GET LOWEST ORDER DIGIT
0586 5F            MOV      E,A
0587 3A1B18        LDA      BCDSAVE+3          ; GET SECOND ORDER DIGIT
058A 07            RLC
058B 07            RLC
058C 07            RLC
058D 07            RLC                         ; ROTATE TO UPPER NIBBLE
058E B3            ORA      E                  ; MERGE WITH LSD
058F 5F            MOV      E,A
0590 3A1A18        LDA      BCDSAVE+2          ; GET THIRD ORDER DIGIT
0593 57            MOV      D,A
0594 CDB005        CALL     DISPLAY            ; SHOW DE DIGITS
0597 D1            POP      D
0598 C9            RET

0599 D5    SHOWMSD:PUSH     D
059A 3A1A18        LDA      BCDSAVE+2          ; GET THIRD ORDER DIGIT
059D 5F            MOV      E,A
059E 3A1918        LDA      BCDSAVE+1          ; GET FOURTH ORDER DIGIT
05A1 07            RLC
05A2 07            RLC
05A3 07            RLC
05A4 07            RLC
05A5 B3            ORA      E
05A6 5F            MOV      E,A
05A7 3A1818        LDA      BCDSAVE            ; GET HIGEST ORDER DIGIT
05AA 57            MOV      D,A
05AB CDB005        CALL     DISPLAY
05AE D1            POP      D
05AF C9            RET
                   ; DISPLAY IS A ROUTINE TO SHOW BCD DIGITS FROM THE
                   ; DE REGISTER PAIR ON THE MONITOR LED DIGITS WITHOUT
                   ; DISTURBING THE A - D CONTROL LINES.
                   ; DESTROYS A,& PSW

DISPLAY:
05B0 3A0E18        LDA      AVGFLG             ; SEE IF SECOND DISPLAY
05B3 FEFF          CPI      0FFH               ; IS TO BE USED
05B5 CACD05        JZ       DISPLAY2
05B8 DB00          IN       CNTRLPT            ; READ CONTROL PORT BITS
05BA E6FD          ANI      1111$1101B         ; SET B1 TO 0 TO TURN ON
05BC D300          OUT      CNTRLPT            ; MAIN DISPLAY
           DISPLAY1:
05BE 7B            MOV      A,E                ; GET LSD'S
05BF D319          OUT      LSDPT              ; SHOW THEM
05C1 7A            MOV      A,D                ; GET MSD BYTE
05C2 E60F          ANI      0000$1111B         ; CLEAR 1,000'S DIGIT
05C4 57            MOV      D,A                ; PUT BACK IN D
05C5 DB1A          IN       MSDPT              ; READ MSD PORT
05C7 E6F0          ANI      1111$0000B         ; MASK OFF OLD DIGIT
05C9 B2            ORA      D                  ; MERGE WITH NEW DIGIT
05CA D31A          OUT      MSDPT              ; SHOW IT
05CC C9            RET
           DISPLAY2:
05CD DB00          IN       CNTRLPT            ; READ CONTROL PORT BITS
05CF F602          ORI      0000$0010B         ; BIT TO SWITCH
05D1 D300          OUT      CNTRLPT            ; TO SECOND DISPLAY
05D3 C3BE05        JMP      DISPLAY1
```

```
                ; DEBOUNCE IS A SOFTWARE DELAY TIMER TO ALLOW SWITCH
                ; CLOSURE TIME.
                ; DESTROYS NOTHING

DEBOUNCE:
05D6  F5                PUSH    PSW
05D7  D5                PUSH    D
05D8  113705            LXI     D,0537H         ; LOAD DE WITH DELAY VALUE
05DB  CDE105            CALL    DELAY           ; (537H = 10 MS DELAY)
05DE  D1                POP     D
05DF  F1                POP     PSW
05E0  C9                RET

; DELAY IS A SOFTWARE DELAY TIMER WHOSE TIME VALUE
                ; IS DETERMINED BY THE DE REGISTER PAIR.
                ; DESTROYS A,PSW,& DE

05E1  1B        DELAY:  DCX     D
 E2   7A                MOV     A,D
 E3   B3                ORA     E
 E4   C2E105            JNZ     DELAY
 E7   C9                RET

E8                     END     START
```

The invention has been described herein in considerable detail, in order to comply with the Patent Statutes and to provide those skilled in the art with information needed to apply the novel principles, and to construct and use such specialized components as are required. However, it is to be understood that the invention can be carried out by specifically different equipment and devices and that various modifications, both as to equipment details and operating procedures, can be effected without departing from the scope of the invention itself.

The invention has been described herein in considerable detail, in order to comply with the Patent Statutes and to provide those skilled in the art with information needed to apply the novel principles, and to construct and use such specialized components as are required. However, it is to be understood that the invention can be carried out by specifically different equipment and devices and that various modifications, both as to equipment details and operating procedures, can be effected without departing from the scope of the invention itself.

The embodiments of the invention in which an exclusive property or privilege is claimed are defined as follows:

1. A method of providing heart rate and blood pressure product information of a primate comprising: sensing the heart rate of a primate, providing a first signal related to the sensed heart rate, sensing the systolic blood pressure of the primate simultaneously with the sensing of the heart rate of the primate, providing a second signal related to the systolic blood pressure simultaneously with the first signal, combining the first and second signals to produce current heart rate and systolic blood pressure product information and time delayed heart rate and systolic blood pressure product information, visually displaying current heart rate and systolic product information and time average heart rate and systolic product information derived from the combined first and second signals, and actuating a recognizable alarm when the time average heart rate and systolic blood pressure information exceed a selected level.

2. The method of claim 1 wherein:
the time average heart rate and systolic blood pressure product information is periodically updated.

3. The method of claim 2 wherein:
the time average is about a two minute average which is updated in about 10 second intervals.

4. The method of claim 1 wherein:
the first and second signals are combined and coordinated with a micropressor programmed to produce current heart rate and systolic blood pressure product information and a timed average heart rate and systolic blood pressure product information.

5. The method of claim 4 wherein:
the program of the microprocessor is characterized with a heart rate and systolic blood pressure product information level determined by the heart rate and systolic blood pressure of the primate.

6. The method of claim 4 wherein:
the time average heart rate and systolic blood pressure product information is periodically updated.

7. The method of claim 1 wherein:
an audible alarm is actuated when the heart rate and blood pressure exceeds a selected level.

8. The method of claim 1 wherein:
the current heart rate and blood pressure product information and time average heart rate and blood pressure product information are simultaneously presented on separate displays.

9. The method of claim 8 wherein:
the current and time product information are each present on a digital read-out display.

10. A method of providing heart rate and blood pressure product information of a primate comprising: sensing the heart rate of a primate, providing a first signal related to the sensed heart rate, sensing the blood pressure of the primate, providing a second signal related to the sensed blood pressure, coordinating the first and second signals to provide a product signal of said first and second signals, and providing readable data of current heart rate and blood pressure product information and time average heart rate and blood pressure product information derived from the product signal.

11. The method of claim 10 including:
simultaneously sensing the heart rate and blood pressure of the primate and simultaneously providing the first signals and second signals.

12. The method of claim 10 wherein:
the systolic blood pressure of the primate is sensed.

13. The method of claim 10 wherein:
the first and second signals are coordinated with a microprocessor programmed to produce current heart rate and blood pressure product information and a timed average heart rate and blood pressure product information.

14. The method of claim 13 wherein:
the program of the microprocessor is characterized with a heart rate and blood pressure product information level determined by the heart rate and blood pressure of the primate.

15. The method of claim 13 wherein:
an audible alarm is actuated when the heart rate and blood pressure exceeds a selected level.

16. The method of claim 13 wherein:
the time average heart rate and blood pressure product information is periodically updated.

17. The method of claim 16 wherein:
the time average is about two minutes which is updated in about 10 second intervals.

18. The method of claim 13 wherein:
the current heart rate and blood pressure product information time average heart rate and blood pressure product information are simultaneously presented on separate displays.

19. The method of claim 18 wherein:
the current and time product information are each present on a digital read-out display.

20. A method of providing heart rate and blood pressure product information of a primate comprising:
sensing the heart rate of a primate, providing a first signal related to the sensed heart rate, sensing the blood pressure of the primate simultaneously with the sensing of the heart rate, providing a second signal related to the sensed blood pressure, combining the first and second signals to produce a product signal of said first and second signals and visually displaying current heart rate and blood pressure product information and time average heart rate and blood pressure product information derived from the product signal.

21. The method of claim 20 wherein:
the time average heart rate and blood pressure product information is periodically updated.

22. The method of claim 21 wherein:
the time average is about a two minute average which is updated in about 10 second intervals.

23. The method of claim 20 wherein:
the systolic blood pressure of the primate is sensed.

24. The method of claim 20 wherein:
the first and second signals are combined and coordinated with a microprocessor programmed to produce current heart rate and blood pressure product information and a timed average heart rate and blood pressure product information.

25. The method of claim 24 wherein:
the program of the microprocessor is characterized with a heart rate and blood pressure product information level determined by the heart rate and blood pressure of the primate.

26. The method of claim 24 wherein:
the time average heart rate and blood pressure product information is periodically updated.

27. The method of claim 20 including:
an audible alarm which is actuated when the heart rate and blood pressure exceeds a selected level.

28. The method of claim 20 wherein:
the current heart rate and blood pressure product information, time average heart rate and blood pressure product information are simultaneously presented on separate displays.

29. The method of claim 28 wherein:
the current and time product information are each present on a digital read-out display.

30. In combination: first means for monitoring the heart rate of a primate and generating a first signal relating to the heart rate, second means for monitoring the blood pressure of the primate simultaneously with the monitoring of the heart rate and generating a second signal related to systolic blood pressure, and an apparatus operatively coupled to said first and second means to receive said first and second signals, said apparatus having means for providing a product of said first and second signals and utilizing the product of said first and second signals to present current heart rate and blood pressure product information and a time average heart rate and blood pressure product information.

31. The structure of claim 30 wherein:
said first means is an EKG monitor having said first signal, and said second means is a blood pressure monitor providing said second signal.

32. The structure of claim 30 wherein:
said means of the apparatus includes display means having digital displays for visually presenting the current heart rate and blood pressure product information and time average heart rate and blood pressure product information.

33. The structure of claim 30 wherein:
said means of the apparatus includes first display means having digital displays for visually presenting the current heart rate and blood pressure product information and said means for displaying said average information including second display means having second digital displays for visually presenting the time average heart rate and blood pressure product information.

34. The structure of claim 30 wherein:
said apparatus includes second means to continuously update said time average information.

35. The structure of claim 34 wherein:
said second means provides an updated two-minute average heart rate and blood pressure product information.

36. The structure of claim 30 wherein:
said apparatus includes alarm means operable to produce an alarm signal when the time average heart rate and blood pressure product information exceeds a selected value.

37. In combination: EKG monitor means for monitoring the heart rate of a primate and generating a first signal relating to the heart rate, blood pressure monitor means for monitoring the blood pressure of said primate simultaneously with the monitoring of the heart rate and generating a second signal related to systolic blood pressure, and an apparatus operatively coupled to said EKG monitor and blood pressure monitor means to receive said first and second signals, said apparatus having microprocessor means accommodating said first and second signals and providing a current product information and time average heart rate and blood pressure product information of said first and second signals, display means associated with the microprocessor means to visually display current heart rate and blood pressure product information and to visually display time average heart rate and blood pressure product information, and alarm means operable to produce an alarm signal when the time average heart rate and blood pressure product information exceeds a selected level.

38. The structure of claim 37 wherein:
said display means includes a first display for visually presenting current heart rate and blood pressure product information and a second display for visually presenting time average heart rate and blood pressure product information.

39. The structure of claim 38 wherein:
said first display is a first digital display for visually presenting in digit form the current heart rate and blood pressure product information, and said second display is a second digital display for visually presenting in digital form time average heart rate and blood pressure product information.

40. The structure of claim 37 wherein:
said microprocessor means includes means to periodically update said time average heart rate and blood pressure product information.

41. The structure of claim 40 wherein:
said means to periodically update said time average heart rate and blood pressure product information operates about every 10 seconds to update said time average heart rate and blood pressure product information.

42. The structure of claim 37 wherein:
said microprocessor means includes means operable to provide about a two-minute average product of the time average product information.

43. The structure of claim 41 wherein:
said microprocessor means includes means to periodically update said time average heart rate and blood pressure product information.

44. The structure of claim 42 wherein:
said means to periodically update said time average heart rate and blood pressure product information operates about every 10 seconds to update said time average heart rate and blood pressure product information.

45. The structure of claim 37 wherein:
said microprocessor means includes means to preset the level of the time average heart rate and blood pressure product information at which the alarm means will operate.

46. An apparatus for monitoring and displaying heart rate and blood pressure product information used with means for monitoring the heart rate of a primate and producing a first signal relating to the heart rate, and means for monitoring the blood pressure of said primate and producing a second signal relating to the blood pressure comprising:
first means accommodating said first and second signals and providing a current heart rate and blood pressure product information and a time average heart rate and blood pressure product information, display means associated with the first means to visually display current heart rate and blood pressure product information and to visually display time average heart rate and blood pressure product information derived from said product signal, and alarm means operable to produce an alarm signal when the time average heart rate and blood pressure product information exceeds a selected level.

47. The apparatus of claim 46 wherein:
said display means includes a first display for visually presenting current heart rate and blood pressure product information, and a second display for visually presenting time average heart rate and blood pressure product information.

48. The apparatus of claim 47 wherein:
said first display is a first digital display for visually presenting in digit form the current heart rate and blood pressure product information, and said second display is a second digital display for visually presenting in digit form time average heart rate and blood pressure product information.

49. The apparatus of claim 47 wherein:
said microprocessor means includes means to periodically update said time average heart rate and blood pressure product information.

50. The apparatus of claim 49 wherein:
said means to periodically update said time average heart rate and blood pressure product information operates about every 10 seconds to update said time average heart rate and blood pressure product information.

51. The apparatus of claim 50 wherein:
said microprocessor means includes means operable to provide about a two-minute average product of the time average product information.

52. The apparatus of claim 47 wherein:

said microprocessor means includes means to periodically update said time average heart rate and blood pressure product information.

53. The apparatus of claim 52 wherein:
said means to periodically update said time average heart rate and blood pressure product information operates about every 10 seconds to update said time average heart rate and blood pressure product information.

54. The apparatus of claim 47 wherein:
said microprocessor means includes means to preset the level of the time average heart rate and blood pressure product information at which the alarm means will operate.

55. An apparatus for monitoring and displaying heart rate and blood pressure product information used with means for monitoring the heart rate of a primate and producing a first signal relating to the heart rate, and means for monitoring the blood pressure of said primate and producing a second signal relating to the blood pressure comprising:
first means accommodating said first and second signals and providing a time average heart rate and blood pressure product signal, display means associated with the first means to visually display the time average heart rate and blood pressure product information derived from said product signal, and alarm means operable to produce an alarm signal when the time average heart rate and blood pressure product information exceeds a selected level.

56. The apparatus of claim 55 wherein:
said first means is a microprocessor programmed to accommodate the first and second signals and provide a product signal relating to the product of the heart rate and blood pressure of the primate.

57. The apparatus of claim 56 wherein:
said microprocessor includes means to preset the level of the time average heart rate and blood pressure product information at which the alarm means will operate.

58. The apparatus of claim 56 wherein:
said display means includes a digital display for visually presenting the time average heart rate and blood pressure product information.

59. The structure of claim 56 wherein:
said microprocessor includes means to periodically update said time average heart rate and blood pressure product information.

60. The apparatus of claim 59 wherein:
said means to periodically update said time average heart rate and blood pressure product information operates about every 10 seconds to update said time average heart rate and blood pressure product information.

61. The apparatus of claim 56 wherein:
said microprocessor includes means operable to provide about a two-minute average product of the time average product information.

62. The apparatus of claim 55 wherein:
said display means includes a digital display for visually presenting in digit form the time average heart rate and blood pressure product information.

* * * * *

UNITED STATES PATENT AND TRADEMARK OFFICE
CERTIFICATE OF CORRECTION

PATENT NO. : 4,404,974
DATED : September 20, 1983
INVENTOR(S) : John S. Titus

It is certified that error appears in the above-identified patent and that said Letters Patent is hereby corrected as shown below:

Column 2, line 67, "7-bits" should be -- 7-bit --.

Column 4, line 36, "filer" should be -- filter --.

Column 6, line 1, "an an" should be -- and an --.

Column 6, line 19, after "and", delete "as shown".

Column 6, line 19, after "87", insert -- as shown --.

Column 10, line 8, "terinal" should be -- terminal --.

Signed and Sealed this

Fifteenth Day of May 1984

[SEAL]

Attest:

GERALD J. MOSSINGHOFF

*Attesting Officer*     *Commissioner of Patents and Trademarks*